United States Patent [19]

Nagai et al.

[11] 4,213,775

[45] Jul. 22, 1980

[54] DIPHENYL ETHER DERIVATIVES AND HERBICIDAL COMPOSITIONS CONTAINING THE SAME

[75] Inventors: Shigeki Nagai; Hakobu Sekioka; Mitsuaki Takenaka; Masazumi Sakata; Yosio Kawaguchi; Seiji Takamura; Minoru Nishimura, all of Ube, Japan

[73] Assignee: Ube Industries, Ltd., Ube, Japan

[21] Appl. No.: 6,919

[22] Filed: Jan. 26, 1979

Related U.S. Application Data

[63] Continuation-in-part of Ser. No. 926,022, Jul. 19, 1978, abandoned.

[30] Foreign Application Priority Data

Jul. 28, 1977 [JP] Japan .................................. 52-89729
Nov. 10, 1978 [JP] Japan ................................ 53-137921

[51] Int. Cl.² ................ C07C 143/833; C07C 143/83; C07C 143/78; A01N 9/30
[52] U.S. Cl. .................................... 71/103; 260/543 R; 260/553 D; 260/556 B; 560/13
[58] Field of Search ........ 260/556 B, 556 AC, 553 D; 560/13; 71/103, 100

[56] References Cited

U.S. PATENT DOCUMENTS

| | | | |
|---|---|---|---|
| 2,986,573 | 5/1961 | Topliss | 260/556 B |
| 3,420,892 | 1/1969 | Martin | 71/103 |
| 3,776,961 | 12/1973 | Theissen | 71/103 |
| 3,784,635 | 1/1974 | Theissen | 71/103 |
| 3,799,760 | 3/1974 | Stephens | 560/13 |
| 3,953,489 | 4/1976 | Tamura | 71/100 |
| 4,071,351 | 1/1978 | Arneklev | 260/556 AC |
| 4,093,446 | 6/1978 | Bayer | 71/103 |
| 4,106,925 | 8/1978 | Rohr | 560/13 |

*Primary Examiner*—Norman Morgenstern
*Assistant Examiner*—Michael Shippen
*Attorney, Agent, or Firm*—Frishauf, Holtz, Goodman & Woodward

[57] ABSTRACT

New diphenyl ether derivatives having one to three substituents selected from a halogen atom and a trifluoromethyl group at any optional one to three positions of the 2'-, 3'-, 4'-, 5'- and 6'-positions in one phenyl moiety and nitro group at the 4-position and unsubstituted or substituted aminosulfonyl group at the 3-position in another phenyl moiety. They have a superior herbicidal effect and can be prepared starting from a known 3-benzylmercapto compound through three steps.

10 Claims, No Drawings

DIPHENYL ETHER DERIVATIVES AND HERBICIDAL COMPOSITIONS CONTAINING THE SAME

This application is a continuation-in-part of U.S. Ser. No. 926,022 filed on July 19, 1978 now abandoned.

This invention relates to a new group of diphenyl ether derivatives, to a process for preparing the same and also to the new use of the said diphenyl ether derivatives as a herbicide.

More particularly, it is concerned with a new diphenyl ether derivative having the formula

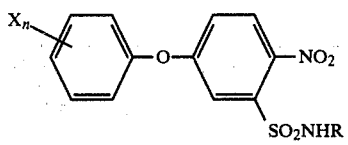

wherein X is a halogen atom or a trifluoromethyl group, n is an integer of 1 to 3 inclusive and; R is a hydrogen atom, a lower alkoxycarbonyl group, an acetyl group, a chloroacetyl group, an N,N-dimethylcalbamoyl group, a lower-alkyl group, a lower-alkenyl group or a benzoyl group, as well as with a process for preparing the said diphenyl ether derivative and a herbicidal composition containing as an active ingredient at least one of the above-defined diphenyl ether derivatives.

In the above formula (I), a halogen atom represented by X may be exemplified by chlorine, bromine, fluorine or iodine; and R may be illustrated by a hydrogen atom, a lower alkoxycarbonyl group, preferably of 1 to 3 carbon atoms in the alkoxy moiety, e.g., methoxycarbonyl, ethoxycarbonyl, n-propoxycarbonyl, isopropoxycarbonyl; an acetyl group; a chloroacetyl group; an N,N-dimethylcarbamoyl group; a lower-alkyl group, preferably of 1 to 4 carbon atoms, e.g., methyl, ethyl, n-propyl, isopropyl, n-butyl; a lower-alkenyl group, preferably of 2 to 4 carbon atoms, e.g., vinyl, allyl, butenyl; or a benzoyl group. Also, where n is an integer of 2 or 3, X's may be the same or different.

It is also to be noted that the diphenyl ether derivatives (I) of this invention are intended to include the corresponding alkali metal salts, in particular sodium salts.

There have been heretofore proposed a wide variety of diphenyl ether derivatives as agricultural herbicides and a considerable number of them has been on the market for practical use. For example, such herbicides as "NIP" (active ingredient: 2',4'-dichloro-4-nitrodiphenyl ether), "CNP" (active ingredient: 2',4',6'-trichloro-4-nitrodiphenyl ether) and "TOPE" (active ingredient: 3'-methyl-4-nitrodiphenyl ether) may be mentioned. These previously known diphenyl ether type herbicides can generally show a superior herbicidal effect in soil treatment against annual weeds of the family Gramineae developed in a paddy field, but they have a common characteristic of having an inferior herbicidal effect against various weeds in foliar treatment or annual broad-leaved weeds and perennial weeds. Further, it can be frequently seen in those derivatives of such a type that differences in their chemical structures such as those in the type, number or position of substituents, may unexpectedly result in differences in whether a herbicidal effect may be exerted, how high the herbicidal effect may be, how rapidly the herbicidal effect may be developed or what the phytotoxicity may be to crops and so on.

The present inventors have made earnest studies to find out new diphenyl ether derivatives having a commercial usefulness and, as a result, they have successfully synthesized a new group of the diphenyl ether derivatives of the above formula (I) and also found such new diphenyl ether derivatives (I) can show a remarkable herbicidal effect against various weeds, without any phytotoxicity to crops and toxicity to human beings and domestic animals as well as fish and shellfishes, and do not have any other harmful properties such as a nasty smell and the like. This invention has been, therefore, completed upon these findings.

The diphenyl ether derivatives (I) of this invention can show a superior weed-killing activity by pre- and post-emergence treatment in soil; in other words, they have both soil treating activities and foliar treating activities. Then, they are effective against various weeds such as annual or perennial weeds of the family Gramineae growing in a paddy or upland field, broad-leaved weeds and the like.

Accordingly, the herbicidal diphenyl ether derivatives (I) of this invention can be effectively applied to a paddy field as a pre-emergent herbicide before or after rice planting or a post-emergent herbicide against perennial weeds or broad-leaved weeds after 1-2 weeks from rice planting, and, further, they can be effectively employed as a soil treatment herbicide before or after sowing in an upland field or as a foliar treatment herbicide against various weeds in an orchard, a tea garden, a mulberry field or non-crop land. In addition, the diphenyl ether derivatives (I) of this invention has a particular characteristic that they can exert an extremely high herbicidal activity against weeds of the family Caryophyllaceae which those previously known diphenyl ether type derivatives could not control.

It is, accordingly, a primary object of this invention to provide new diphenyl ether derivatives of the above formula (I) which show an excellent herbicidal effect.

Another object of this invention is to provide a process for preparing the above-mentioned diphenyl ether derivatives.

A further object of this invention is to provide a herbicidal composition which comprises as an active ingredient at least one of the diphenyl ether derivatives (I).

According to one aspect of this invention, there is provided a group of new diphenyl ether derivative of the above formula (I). Representative examples of the diphenyl ether derivatives (I) are given in the following Table I for illustrating purpose only.

As explained above, alkali metal salts of the diphenyl ether derivatives (I) also fall within the scope of this invention and, as illustrative examples, sodium salt of 2',4',6'-trichloro-3-methoxycarbonylaminosulfonyl-4-nitrodiphenyl ether and sodium salt of 2',4'-dichloro-3-methoxycarbonylaminosulfonyl-4-nitrodiphenyl ether are given in Table 1, designated as Compound No. 25 and No. 36, respectively.

Among the diphenyl ether derivatives according to this invention, compounds represented by formula (I) wherein $X_n$ represents a 2,4-dichloro-, 2,4,6-trichloro-, 2,4-dichloro-6-fluoro-, 2-chloro-4-bromo-, 2-chloro-4-trifluoromethyl- or 2-bromo-4-trifluoromethyl substituent, are preferable in view of the herbicidal effect upon perennial weeds, particularly upon "Mizugayatsuri (*Cyperus serotinus* Rottb.)", the price for production and the phytotoxicity.

As particularly preferable compounds may be mentioned 2',4'-dichloro-3-methoxycarbonylaminosulfonyl-4-nitrodiphenyl ether (Compound No. 9), 2',4',6'-trichloro-3-methoxycarbonylaminosulfonyl-4-nitrodiphenyl ether (Compound No. 23), 2',4'-dichloro-6-fluoro-3-methoxycarbonylaminosulfonyl-4-nitrodiphenyl ether (Compound No. 38), 2'-chloro-4'-bromo-3-methoxycarbonylaminosulfonyl-4-nitrodiphenyl ether (Compound No. 47), 2'-chloro-4'-trifluoromethyl-3-methoxycarbonylaminosulfonyl-4-nitrodiphenyl ether (Compound No. 52), 2'-chloro-4'-trifluoromethyl-3-ethoxycarbonylaminosulfonyl-4-nitrodiphenyl ether (Compound No. 53), 2'-chloro-4'-trifluoromethyl-3-acetylaminosulfonyl-4-nitrodiphenyl ether (Compound No. 61), 2'-bromo-4'-trifluoromethyl-3-methoxycarbonylaminosulfonyl-4-nitrodiphenyl ether (Compound No. 70), 2'-bromo-4'-trifluoromethyl-3-N,N-dimethylcarbamoyl aminosulfonyl-4-nitrodiphenyl ether (Compound No. 73).

Table 1

| Compound No. | Chemical Structure | M.P. (°C.) | Analysis (%) Calcd. | Found |
|---|---|---|---|---|
| 1 | Cl-C$_6$H$_4$-O-C$_6$H$_3$(NO$_2$)-SO$_2$NH$_2$ | 110–114 | H 2.76<br>C 43.84<br>N 8.52 | 2.51<br>43.56<br>8.15 |
| 2 | Cl-C$_6$H$_4$-O-C$_6$H$_3$(NO$_2$)-SO$_2$NHCOOCH$_3$ | 163–167 | H 2.87<br>C 43.47<br>N 7.24 | 2.48<br>43.10<br>6.95 |
| 3 | Cl-C$_6$H$_4$-O-C$_6$H$_3$(NO$_2$)-SO$_2$NHCOOC$_2$H$_5$ | 150–154 | H 3.27<br>C 44.95<br>N 6.99 | 3.00<br>44.00<br>6.75 |
| 4 | Cl-C$_6$H$_4$-O-C$_6$H$_3$(NO$_2$)-SO$_2$NHCOOCH(CH$_3$)$_2$ | 149–153 | H 3.64<br>C 46.32<br>N 6.75 | 3.60<br>46.10<br>6.40 |
| 5 | 2,3-Cl$_2$-C$_6$H$_3$-O-C$_6$H$_3$(NO$_2$)-SO$_2$NH$_2$ | 183–186 | H 2.22<br>C 39.68<br>N 7.72 | 2.40<br>39.60<br>7.65 |
| 6 | 2,3-Cl$_2$-C$_6$H$_3$-O-C$_6$H$_3$(NO$_2$)-SO$_2$NHCOOCH$_3$ | 166–170 | H 2.39<br>C 39.92<br>N 6.65 | 2.20<br>40.25<br>6.32 |
| 7 | 2,3-Cl$_2$-C$_6$H$_3$-O-C$_6$H$_3$(NO$_2$)-SO$_2$NHCOOC$_2$H$_5$ | 140–143 | H 2.78<br>C 41.39<br>N 6.44 | 2.80<br>41.70<br>6.10 |
| 8 | 2,4-Cl$_2$-C$_6$H$_3$-O-C$_6$H$_3$(NO$_2$)-SO$_2$NH$_2$ | 95–98 | H 2.22<br>C 39.68<br>N 7.72 | 2.03<br>39.60<br>7.85 |

Table 1-continued

| Compound No. | Chemical Structure | M.P. (°C.) | Analysis (%) Calcd. | Found |
|---|---|---|---|---|
| 9 | Cl-C6H3(Cl)-O-C6H3(NO2)-SO2NHCOOCH3 | 170–172 | H 2.39<br>C 39.92<br>N 6.65 | 2.30<br>39.80<br>6.45 |
| 10 | Cl-C6H3(Cl)-O-C6H3(NO2)-SO2NHCOOC2H5 | 138–140 | H 2.78<br>C 41.39<br>N 6.44 | 2.48<br>41.36<br>6.49 |
| 11 | Cl-C6H3(Cl)-O-C6H3(NO2)-SO2NHCOOCH(CH3)2 | 137–139 | H 3.14<br>C 42.77<br>N 6.24 | 2.99<br>42.57<br>6.25 |
| 12 | Cl-C6H3(Cl)-O-C6H3(NO2)-SO2NHCOCH2Cl | 141–143 | H 2.06<br>C 38.24<br>N 6.37 | 2.00<br>38.01<br>6.20 |
| 13 | Cl-C6H3(Cl)-O-C6H3(NO2)-SO2NHCON(CH3)2 | 188–191 | H 3.02<br>C 41.49<br>N 9.68 | 3.25<br>41.00<br>9.50 |
| 14 | Cl-C6H3(Cl)-O-C6H3(NO2)-SO2NHCOOCH3 | 201–203 | H 2.39<br>C 39.92<br>N 6.65 | 2.45<br>40.00<br>6.41 |
| 15 | Cl-C6H3(Cl)-O-C6H3(NO2)-SO2NHCOOC2H5 | 193–196 | H 2.78<br>C 41.39<br>N 6.44 | 3.00<br>41.30<br>6.32 |
| 16 | 2,6-Cl2-C6H3-O-C6H3(NO2)-SO2NH2 | 133–136 | H 2.22<br>C 39.68<br>N 7.72 | 2.10<br>39.71<br>7.45 |
| 17 | 2,3,5-Cl3-C6H2-O-C6H3(NO2)-SO2NH2 | 164–168 | H 1.78<br>C 36.24<br>N 7.05 | 1.85<br>36.60<br>6.90 |

Table 1-continued

| Compound No. | Chemical Structure | M.P. (°C.) | Analysis (%) Calcd. | Found |
|---|---|---|---|---|
| 18 | 2,4,5-trichlorophenyl 4-nitro-3-sulfamoylphenyl ether | 166–168 | H 1.78<br>C 36.24<br>N 7.05 | 1.75<br>36.40<br>6.85 |
| 19 | 2,4,5-trichlorophenyl 4-nitro-3-(methoxycarbonylsulfamoyl)phenyl ether | 189–192 | H 1.99<br>C 36.90<br>N 6.15 | 2.00<br>37.00<br>6.00 |
| 20 | 2,4,5-trichlorophenyl 4-nitro-3-(ethoxycarbonylsulfamoyl)phenyl ether | 156–158 | H 2.36<br>C 38.35<br>N 5.97 | 2.45<br>38.40<br>5.30 |
| 21 | 2,4,5-trichlorophenyl 4-nitro-3-(isopropoxycarbonylsulfamoyl)phenyl ether | 148–151 | H 2.71<br>C 39.73<br>N 5.79 | 2.60<br>40.00<br>5.25 |
| 22 | 2,4,6-trichlorophenyl 4-nitro-3-sulfamoylphenyl ether | 125–128 | H 1.78<br>C 36.24<br>N 7.05 | 1.90<br>36.00<br>6.90 |
| 23 | 2,4,6-trichlorophenyl 4-nitro-3-(methoxycarbonylsulfamoyl)phenyl ether | 189–192 | H 1.99<br>C 36.90<br>N 6.15 | 2.00<br>36.75<br>6.01 |
| 24 | 2,4,6-trichlorophenyl 4-nitro-3-(ethoxycarbonylsulfamoyl)phenyl ether | 184–186 | H 2.36<br>C 38.35<br>N 5.97 | 2.10<br>38.17<br>5.85 |
| 25 | 2,4,6-trichlorophenyl 4-nitro-3-(methoxycarbonylsulfamoyl sodium salt)phenyl ether | With decomp. above 105° C. | H 1.69<br>C 35.20<br>N 5.87 | 1.70<br>34.90<br>5.57 |
| 26 | 2,4,6-trichlorophenyl 4-nitro-3-(N,N-dimethylaminocarbonylsulfamoyl)phenyl ether | 186–190 | H 2.58<br>C 38.43<br>N 8.97 | 2.45<br>38.05<br>8.40 |

Table 1-continued

| Compound No. | Chemical Structure | M.P. (°C.) | Analysis (%) Calcd. | Found |
|---|---|---|---|---|
| 27 | 2,4,6-trichlorophenyl 4-nitro-3-(N-acetylsulfamoyl)phenyl ether | 214–219 | H 2.06<br>C 38.24<br>N 6.37 | 2.10<br>28.00<br>6.05 |
| 28 | 4-bromophenyl 4-nitro-3-sulfamoylphenyl ether | 117–120 | H 2.43<br>C 38.62<br>N 7.51 | 2.40<br>38.00<br>7.10 |
| 29 | 4-bromophenyl 4-nitro-3-(N-methoxycarbonylsulfamoyl)phenyl ether | 155–156 | H 2.57<br>C 38.99<br>N 6.50 | 2.35<br>38.35<br>6.05 |
| 30 | 4-bromophenyl 4-nitro-3-(N-ethoxycarbonylsulfamoyl)phenyl ether | 130–133 | H 2.94<br>C 40.46<br>N 6.29 | 2.70<br>40.06<br>5.95 |
| 31 | 4-bromophenyl 4-nitro-3-(N-isopropoxycarbonylsulfamoyl)phenyl ether | 148–150 | H 3.29<br>C 41.84<br>N 6.10 | 3.25<br>41.70<br>5.85 |
| 32 | 2,4-dibromophenyl 4-nitro-3-sulfamoylphenyl ether | 155–158 | H 1.78<br>C 31.88<br>N 6.20 | 1.85<br>32.28<br>5.85 |
| 33 | 2,4-dibromophenyl 4-nitro-3-(N-methoxycarbonylsulfamoyl)phenyl ether | 167–172 | H 1.98<br>C 32.96<br>N 5.49 | 1.90<br>33.20<br>5.15 |
| 34 | 2,4-dibromophenyl 4-nitro-3-(N-ethoxycarbonylsulfamoyl)phenyl ether | 162–164 | H 2.31<br>C 34.37<br>N 5.35 | 2.50<br>34.40<br>5.25 |
| 35 | 2,4-dibromophenyl 4-nitro-3-(N-isopropoxycarbonylsulfamoyl)phenyl ether | 143–145 | H 2.62<br>C 35.71<br>N 5.21 | 2.55<br>36.02<br>4.90 |

Table 1-continued

| Compound No. | Chemical Structure | M.P. (°C.) | Analysis (%) Calcd. | Found |
|---|---|---|---|---|
| 36 | 2,4-dichlorophenyl-(4-nitro-3-(SO$_2$N(Na$^+$)COOCH$_3$))phenyl ether | 77-99 | H 2.05<br>C 37.94<br>N 6.32 | 1.95<br>37.70<br>6.25 |
| 37 | 2,4-dichloro-6-fluorophenyl-(4-nitro-3-sulfamoyl)phenyl ether | 128-132 | H 1.85<br>C 37.81<br>N 7.35 | 2.05<br>38.45<br>7.05 |
| 38 | 2,4-dichloro-6-fluorophenyl-(4-nitro-3-(SO$_2$NHCOOCH$_3$))phenyl ether | 152-156 | H 2.07<br>C 38.28<br>N 6.38 | 2.05<br>38.40<br>6.10 |
| 39 | 2,4-dichloro-6-fluorophenyl-(4-nitro-3-(SO$_2$NHCOOC$_2$H$_5$))phenyl ether | 151-154 | H 2.45<br>C 39.75<br>N 6.18 | 2.40<br>40.05<br>5.85 |
| 40 | 2,4-dichloro-6-fluorophenyl-(4-nitro-3-(SO$_2$NHCOOCH(CH$_3$)$_2$))phenyl ether | 152-156 | H 2.80<br>C 41.12<br>N 6.00 | 2.75<br>41.25<br>6.00 |
| 41 | 2,4-dichloro-6-fluorophenyl-(4-nitro-3-(SO$_2$NHCOCH$_3$))phenyl ether | 176-180 | H 2.14<br>C 39.73<br>N 6.62 | 2.20<br>40.20<br>6.45 |
| 42 | 2,4-dichloro-6-fluorophenyl-(4-nitro-3-(SO$_2$NHCOCH$_2$Cl))phenyl ether | 203-206 | H 1.76<br>C 36.74<br>N 6.12 | 1.85<br>36.55<br>6.00 |
| 43 | 2,4-dichloro-6-fluorophenyl-(4-nitro-3-(SO$_2$NHCON(CH$_3$)$_2$))phenyl ether | 168-173 | H 2.68<br>C 39.83<br>N 9.29 | 2.65<br>39.35<br>9.05 |
| 44 | 4-fluorophenyl-(4-nitro-3-sulfamoyl)phenyl ether | 117-121 | H 2.90<br>C 46.15<br>N 8.97 | 2.70<br>45.85<br>8.65 |

Table 1-continued

| Compound No. | Chemical Structure | M.P. (°C.) | Analysis (%) Calcd. | Found |
|---|---|---|---|---|
| 45 | F-C6H4-O-C6H3(NO2)(SO2NHCOOCH3) | 192–196 | H 2.99<br>C 45.40<br>N 5.45 | 2.75<br>45.15<br>5.20 |
| 46 | 2-Cl-4-Br-C6H3-O-C6H3(NO2)(SO2NH2) | 151–153 | H 1.98<br>C 35.35<br>N 6.87 | 2.10<br>35.80<br>6.70 |
| 47 | 2-Cl-4-Br-C6H3-O-C6H3(NO2)(SO2NHCOOCH3) | 162–163 | H 2.16<br>C 36.11<br>N 6.02 | 2.15<br>36.20<br>5.85 |
| 48 | 2-Cl-4-Br-C6H3-O-C6H3(NO2)(SO2NHCOOC2H5) | 132–134 | H 2.52<br>C 37.55<br>N 5.84 | 2.40<br>37.50<br>5.65 |
| 49 | 2-Cl-4-Br-C6H3-O-C6H3(NO2)(SO2NHCOOCH(CH3)2) | 152–154 | H 2.86<br>C 38.92<br>N 5.68 | 2.60<br>39.00<br>5.50 |
| 50 | 2-Cl-4-Br-C6H3-O-C6H3(NO2)(SO2NHCON(CH3)2) | 194–197 | H 2.82<br>C 38.77<br>N 6.03 | 2.55<br>38.95<br>7.80 |
| 51 | 2-Cl-4-CF3-C6H3-O-C6H3(NO2)(SO2NH2) | 118–121 | H 2.02<br>C 39.35<br>N 7.06 | 1.98<br>39.10<br>7.03 |
| 52 | 2-Cl-4-CF3-C6H3-O-C6H3(NO2)(SO2NHCOOCH3) | 127–130 | H 2.22<br>C 39.61<br>N 6.16 | 2.10<br>39.35<br>6.20 |
| 53 | 2-Cl-4-CF3-C6H3-O-C6H3(NO2)(SO2NHCOOC2H5) | 124–126 | H 2.59<br>C 40.99<br>N 5.98 | 2.39<br>40.81<br>6.01 |

Table 1-continued

| Compound No. | Chemical Structure | M.P. (°C.) | Analysis (%) Calcd. | Found |
|---|---|---|---|---|
| 54 | CF$_3$—⟨Cl⟩—O—⟨NO$_2$⟩—SO$_2$NHCON(CH$_3$)$_2$ | 149–152 | H 2.81<br>C 41.07<br>N 8.98 | 2.73<br>41.00<br>9.02 |
| 55 | CF$_3$—⟨Cl⟩—O—⟨NO$_2$⟩—SO$_2$NHCH$_3$ | 128–129 | H 2.45<br>C 40.93<br>N 6.82 | 2.51<br>40.82<br>6.90 |
| 56 | CF$_3$—⟨Cl⟩—O—⟨NO$_2$⟩—SO$_2$NHC$_2$H$_5$ | 94–96 | H 2.85<br>C 42.41<br>N 6.60 | 2.80<br>42.50<br>6.45 |
| 57 | CF$_3$—⟨Cl⟩—O—⟨NO$_2$⟩—SO$_2$NH-n-C$_3$H$_7$ | 94–97 | H 3.22<br>C 43.79<br>N 6.39 | 3.50<br>43.51<br>6.28 |
| 58 | CF$_3$—⟨Cl⟩—O—⟨NO$_2$⟩—SO$_2$NH-i-C$_3$H$_7$ | 126–128 | H 3.22<br>C 43.79<br>N 6.39 | 3.48<br>43.59<br>6.51 |
| 59 | CF$_3$—⟨Cl⟩—O—⟨NO$_2$⟩—SO$_2$NH-n-C$_4$H$_9$ | 98–101 | H 3.56<br>C 45.09<br>N 6.19 | 3.81<br>45.11<br>6.30 |
| 60 | CF$_3$—⟨Cl⟩—O—⟨NO$_2$⟩—SO$_2$NHCH$_2$CH=CH$_2$ | 81–84 | H 2.77<br>C 43.99<br>N 6.41 | 2.85<br>43.80<br>5.50 |
| 61 | CF$_3$—⟨Cl⟩—O—⟨NO$_2$⟩—SO$_2$NHCOCH$_3$ | 152–155 | H 2.30<br>C 41.06<br>N 6.39 | 2.30<br>41.25<br>6.30 |
| 62 | CF$_3$—⟨Cl⟩—O—⟨NO$_2$⟩—SO$_2$NHCOCH$_2$Cl | 130–132 | H 1.92<br>C 38.07<br>N 5.92 | 2.00<br>38.45<br>5.70 |

Table 1-continued

| Compound No. | Chemical Structure | M.P. (°C.) | Analysis (%) Calcd. | Found |
|---|---|---|---|---|
| 63 | CF₃–(2-Cl-phenyl)–O–(4-NO₂-phenyl)–SO₂NHCO–C₆H₅ | 191–194 | H 2.42<br>C 47.96<br>N 5.59 | 2.35<br>48.40<br>6.05 |
| 64 | CF₃–(2-Cl-phenyl)–O–(4-NO₂-phenyl)–SO₂NHCOO-i-C₃H₇ | 134–136 | H 2.92<br>C 42.29<br>N 5.80 | 3.00<br>42.25<br>5.50 |
| 65 | (2-CF₃-4-Cl-phenyl)–O–(4-NO₂-phenyl)–SO₂NH₂ | 155–158 | H 2.03<br>C 39.35<br>N 7.06 | 2.00<br>39.45<br>6.75 |
| 66 | (2-CF₃-4-Cl-phenyl)–O–(4-NO₂-phenyl)–SO₂NHCOOCH₃ | 173–176 | H 2.22<br>C 39.61<br>N 6.16 | 2.20<br>39.85<br>6.05 |
| 67 | CF₃–(2-Br-phenyl)–O–(4-NO₂-phenyl)–SO₂NH₂ | 94–97 | H 1.83<br>C 35.39<br>N 6.35 | 1.80<br>35.40<br>6.00 |
| 68 | CF₃–(2-Br-phenyl)–O–(4-NO₂-phenyl)–SO₂NHCH₃ | 122–125 | H 2.21<br>C 36.94<br>N 6.16 | 2.40<br>37.00<br>6.25 |
| 69 | CF₃–(2-Br-phenyl)–O–(4-NO₂-phenyl)–SO₂NHC₂H₅ | 103–105 | H 2.58<br>C 38.39<br>N 5.97 | 2.75<br>38.50<br>6.00 |
| 70 | CF₃–(2-Br-phenyl)–O–(4-NO₂-phenyl)–SO₂NHCOOCH₃ | 127–129 | H 2.02<br>C 36.09<br>N 5.61 | 2.00<br>36.15<br>5.10 |
| 71 | CF₃–(2-Br-phenyl)–O–(4-NO₂-phenyl)–SO₂NHCOOC₂H₅ | 122–124 | H 2.36<br>C 37.43<br>N 5.46 | 2.30<br>37.10<br>5.00 |

Table 1-continued

| Compound No. | Chemical Structure | M.P. (°C.) | Analysis (%) Calcd. | Found |
|---|---|---|---|---|
| 72 | 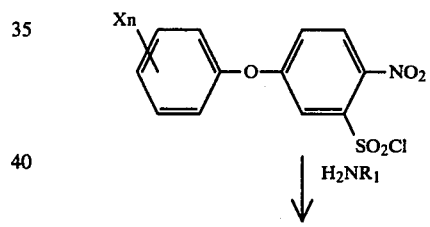 | 124–126 | H 2.68<br>C 38.72<br>N 5.31 | 2.75<br>38.75<br>5.00 |
| 73 | 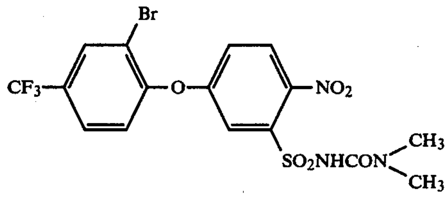 | 160–162 | H 2.56<br>C 37.51<br>N 8.20 | 2.50<br>37.50<br>8.05 |
| 74 | 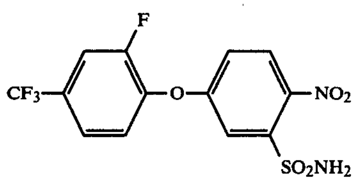 | 97–99 | H 2.12<br>C 40.99<br>N 7.36 | 2.05<br>41.00<br>7.25 |
| 75 | 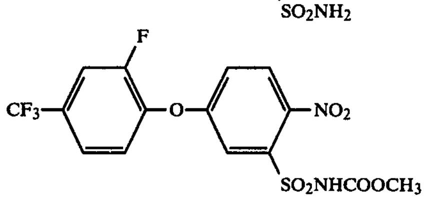 | 135–137 | H 2.30<br>C 41.10<br>N 6.39 | 2.20<br>41.15<br>6.55 |

The diphenyl ether derivatives of this invention can be prepared, according to the following reaction steps.

The 1st step:

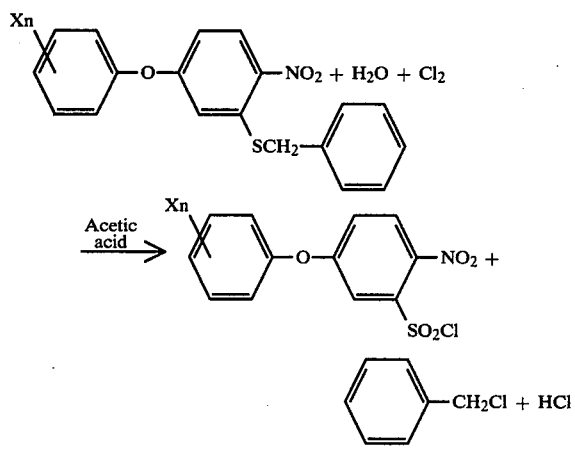

The 2nd step:

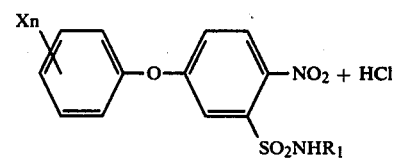

wherein $R_1$ is a hydrogen atom, a lower-alkyl group or a lower-alkenyl group.

The 3rd step:

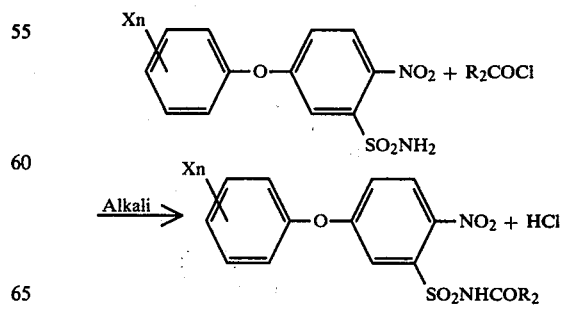

wherein $R_2$ is a lower-alkoxy group, a methyl group, a chloromethyl group, a dimethylamino group or a phenyl group.

In the first step, the sulfonyl chloride can be prepared by introducing chlorine gas into a solution of the starting 3-benzylmercapto compound which can be obtained by a well-known method as illustrated below:

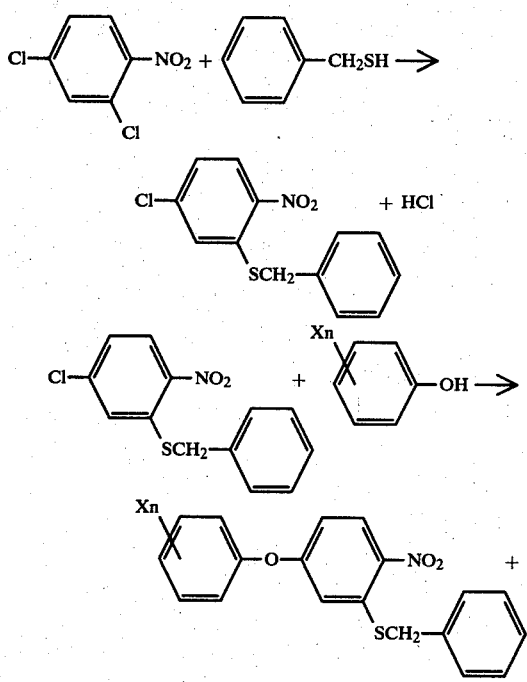

As the solvent may preferably be employed an aqueous acetic acid. The aqueous acetic acid to be used contains 5–50 wt.%, preferably 10–15 wt.% of water. The reaction time may be more than 1 hours, preferably 3–6 hours.

The reaction temperature may preferably be in the range of 10°–15° C. At a higher temperature, substitution on the nucleus tends to occur. The thus produced compound may be recovered from the reaction medium by ordinary procedures.

In the second step, the product in the first step is reacted easily with an excess amount of ammonia, a mono-lower-alkylamine or a mono-lower-alkenylamine. As the solvent for the reaction may be used an organic solvent, e.g., an aromatic solvent such as benzene, toluene, xylene, etc. and an ester such as ethyl acetate, methyl acetate, etc. The desired product in which $R_1$ is a hydrogen atom can also be obtained in high yield without any solvent by adding the starting sulfonyl chloride to a 5–28% aqueous ammonia. The reaction temperature may preferably be maintained at 10°–30° C. with cooling, since the reaction is exothermic.

In the third step, the desired compound of this invention can be obtained by adding an acid chloride to a solution of the starting sulfonamide compound in an organic solvent or an alkaline water in the presence of a base. When the acid chloride is unstable against water or has poor reactivity, the reaction may preferably be conducted by using an organic solvent and by heating the reaction system.

While any organic solvent can be used for the purpose if it does not react with the acid chloride, there may preferably be mentioned as a solvent acetone, dimethylsulfoxide, dimethylformamide, dimethylacetamide, etc. In particular, acetone may most advantageously be employed for the purpose.

As the base, potassium hydroxide and sodium hydroxide may preferably be employed when the reaction is carried out in an aqueous medium. These hydroxides may advantageously be employed as a 1–5 wt% aqueous solution. When the reaction is carried out in an organic medium, potassium carbonate or sodium carbonate may advantageously be used. The reaction is carried out at 10°–20° C. in an alkaline aqueous medium and at a temperature between room temperature and 15° C. in an organic medium. While the reaction period depends on the kind of the reagent to be used, it is in the range of about 1–10 hours.

The desired product can easily be recovered by an ordinary method.

The above-depicted reaction steps will be more fully illustrated by the following examples.

EXAMPLE 1

Synthesis of benzyl-2-nitro-5-chlorophenyl sulfide

To a solution of 86 g. (0.4 mole) of 1-nitro-2,4-dichlorobenzene and 56 g. (0.45 mole) of benzylmercaptan in 1.4 l. of isopropyl alcohol was gradually added dropwise a soultion of 30 g. of potassium hydroxide in 20 ml. of water and 70 ml. of ethanol. After completion of the dropwise addition, the resulting mixture was refluxed on a water bath for 3 hours. After standing overnight, the crystalline substance thus separated was recovered by filtration and then recrystallized from a mixture of ethanol with a small amount of benzene to give 87 g. (yield, 70%) of benzyl-2-nitro-5-chlorophenyl sulfide as yellow prisms of M.P. 131°–134° C.

EXAMPLE 2

Synthesis of 2',4'-dichloro-3-benzylmercapto-4-nitrodiphenyl ether

To a solution of 16.3 g. (0.1 mole) of 2,4-dichlorophenol in 30 ml. of dimethylacetamide were added 5.6 g. (0.1 mole) of potassium hydroxide and then the resulting mixture was heated to 120° C. to dissolve the potassium hydroxide. After it was allowed to cool, 28 g. (0.1 mole) of benzyl-2-nitro-5-chlorophenyl sulfide were added thereto. The resulting mixture was heated at about 155° C. while stirring for 6 hours and then cooled. After addition of water, the oily substance thus separated was extracted with benzene. Thereafter, the extract was washed with a dilute aqueous solution of sodium hydroxide and water, dried over anhydrous sodium sulfate and then the benzene was distilled off. The residue was recrystallied from ethanol to give 27 g. (yield, 67%) of 2',4'-dichloro-3-benzylmercapto-4-nitrodiphenyl ether as yellow powdery crystals of M.P. 104°–105° C.

EXAMPLE 3

Synthesis in the 1st and 2nd steps (1) Synthesis of 2',4'-dichloro-3-aminosulfonyl-4-nitrodiphenyl ether (Compound No. 8)

Into a suspension of 33 g. (0.008 mole) of 2',4'-dichloro-3-benzylmercapto-4-nitrodiphenyl ether in 200 ml. of glacial acetic acid and 30 ml. of water was bubbled chlorine gas while stirring at about 12° C. and the mixture was then left at ordinary temperature overnight. Then, the mixture was poured into water, the oily substance thus separated was extracted with benzene, the extract was washed with water and dried over anhydrous sodium sulfate. The solvent was distilled off to leave 2',4'-dichloro-3-chlorosulfonyl-4-nitdodiphenyl ether as a dark red oily substance.

Then, the product thus obtained was dissolved in ethyl acetate and the resulting solution was added dropwise to ammonia-saturated ethyl acetate. After completion of the dropwise addition, the mixture was stirred at ordinary temperature for 30 minutes and water was added thereto. The resulting mixture was washed with water and dried over anhydrous sodium sulfate. The solvent was distilled off and the residue was recrystallized from ethanol to afford 22.7 g. (yield, 78%) of 2',4'-dichloro-3-aminosulfonyl-4-nitrodiphenyl ether (Compound No. 8) as pale yellow powdery crystals of M.P. 95°-98° C.

(2) Synthesis of 2'-chloro-4'-trifluoromethyl-3-isopropylaminosulfonyl-4-nitrodiphenyl ether (Compound No. 58)

To a suspension of 18.5 g. (0.042 mole) of 2'-chloro-4'-trifluoromethyl-3-benzylmercapto-4-nitrodiphenyl ether in a mixture of 70 ml. of glacial acetic acid with 10 ml. of water was bubbled chlorine gas at 10°-20° C. with stirring over 2 hours to conduct the reaction and then stirring was continued at ordinary temperature for further 1 hour. Thereafter, the content was poured into water, the oily substance thus liberated was extracted with benzene, the extract was washed with water and dehydrated with sodim sulfate and then the solvent was distilled off to afford 2'-chloro-4'-trifluoromethyl-3-chlorosulfonyl-4-nitrodiphenyl ether.

Then, the so obtained product was dissolved in ethyl acetate and the solution was added dropwise to a solution of 5.9 g. (0.1 mole) of isopropylamine in ethyl acetate. After completion of the dropwise addition, the mixture was stirred at ordinary temperature overnight, washed with water and then dehydrated with sodium sulfate. The solvent was distilled off and the residue was recrystallized from ethanol to give 16.3 g. (yield, 89%) of 2'-chloro-4'-trifluoromethyl-3-isopropylaminosulfonyl-4-nitrodiphenyl ether (Compound No. 58) as pale yellow prisms with M.P. 126°-128° C.

(3) Synthesis of 2'-chloro-4'-trifluoromethyl-3-aminosulfonyl-4-nitrodiphenyl ether (Compound No. 51)

Following the procedures of Example 3, (2) above, 2'-chloro-4'-trifluoromethyl-3-chlorosulfonyl-4-nitrodiphenyl ether was synthesized from 15.0 g. (0.034 mole) of 2'-chloro-4'-trifluoromethyl-3-benzylmercapto-4-nitrodiphenyl ether.

Then, the so obtained product was dissolved in ethyl acetate and the solution was added dropwise to an ethyl acetate solution saturated with ammonia. After completion of the dropwise addition, the mixture was stirred at ordinary temperature for 1 hour, washed with water and dehydrated with sodium sulfate. The solvent was distilled off and the residue was recrystallized from isopropanol to give 10.5 g. (yield, 78%) of 2'-chloro-4'-trifluoromethyl-3-aminosulfonyl-4-nitrodiphenyl ether as pale yellow powders with M.P. 117°-120° C. (Compound No. 51).

EXAMPLE 4

Synthesis in the 3rd step (1) Synthesis of 2',4'-dichloro-3-ethoxycarbonylaminosulfonyl-4-nitrodiphenyl ether (Compound No. 10)

To a solution of 3.6 g. (0.01 mole) of 2',4'-dichloro-3-aminosulfonyl-4-nitrodiphenyl ether in 40 ml. of a 1.25 w/v% aqueous solution of sodium hydroxide were added dropwise by turns, while stirring at about 25° C., 3.6 g. (0.033 mole) of ethyl chloroformate and a 10 w/v% aqueous solution of sodium hydroxide to adjust its pH to 10-11. After completion of the dropwise addition, the mixture was stirred for 30 minutes and adjusted to pH 6.5 by the dropwise addition of a dilute aqueous solution of hydrochloric acid. Insoluble materials were filtered off and the filtrate was made acidic with a strong hydrochloric acid. The so separated crystalline substance was recovered by filtration, dried and then recrystallized from benzene to afford 2.5 g. (yield, 57%) of 2',4'-dichloro-3-ethoxycarbonylaminosulfonyl-4-nitrodiphenyl ether (Compound No. 10) as pale yellow prisms of M.P. 138°-140° C.

(2) Synthesis of 2',4'-dichloro-3-chloroacetylaminosulfonyl-4-nitrodiphenyl ether (Compound No. 12)

To a solution of 3.6 g. (0.01 mole) of 2',4'-dichloro-3-aminosulfonyl-4-nitrodiphenyl ether in 2.5 ml. of a 2 w/v% aqueous solution of sodium hydroxide were added dropwise by turns, while stirring at about 20° C., 4.5 g. (0.04 mole) of chloroacetyl chloride and a 10 w/v% aqueous solution of sodium hydroxide to adjust its pH to 10-11. After completion of the dropwise addition, the mixture was stirred for 30 minutes, 200 ml. of water were added thereto to dissolve insoluble materials, the mixture was adjusted its pH to 4 with the dropwise addition of a dilute aqueous solution of hydrochloric acid and then insoluble materials were filtered off. Then, the filtrate was made acidic with a strong hydrochloric acid, the so separated crystalline substance was recovered by filtration, dried and recrystallized from a mixture of benzene with n-hexane to give 3.3 g. (yield, 75%) of 2',4'-dichloro-3-chloroacetylaminosulfonyl-4-nitrodiphenyl ether (Compound No. 12) as pale brown prisms of M.P. 141°-143° C.

(3) Synthesis of sodium salt of 2',4',6'-trichloro-3-methoxycarbonylaminosulfonyl-4-nitrodiphenyl ether (Compound No. 25)

To a solution of 7.2 g. (0.018 mole) of 2',4',6'-trichloro-3-aminosulfonyl-4-nitrodiphenyl ether in 40 ml. of a 2.5 w/v% aqueous solution of sodium hydroxide were added dropwise by turns, while stirring at about 20° C., 7.5 g. (0.08 mole) of methyl chloroformate and a 10 wt.% of aqueous solution of sodium hydroxide to adjust its pH to 10-11. After completion of the dropwise addition, the mixture was stirred for 30 minutes. Then, the so separated substance was recovered by filtration, washed with water, dehydrated and dried to give 6.6 g. (yield, 7.7%) of sodium salt of 2',4',6'-trichloro-3-methoxycarbonylaminosulfonyl-4-nitrodiphenyl ether (Compound No. 25) as colorless powdery crystals of M.P. above 105° C. (with decomp.).

(4) Synthesis of 2',4',6'-trichloro-3-N,N-dimethyl aminocarbonylaminosulfonyl-4-nitrodiphenyl ether (Compound No. 26)

To a solution of 2 g. (0.005 mole) of 2',4',6'-trichloro-3-aminosulfonyl-4-nitrodiphenyl ether in 80 ml. of acetone were added 1.1 g. (0.008 mole) of potassium carbonate and 0.9 g. (0.008 mole) of N,N-dimethylcarbamoyl chloride and the resulting mixture was heated under reflux for 12 hours. Thereafter, the acetone was distilled off, the residue was dissolved in a dilute aqueous solution of sodium hydroxide, the resulting solution was adjusted to pH 5.8 with a dilute hydrochloric acid and insoluble materials were filtered off. The filtrate was made acidic with a strong hydrochloric acid, the so separated crystalline substance was recovered by filtration, dried and recrystallized from a mixture of benzene with n-hexane to give 1 g. (yield, 43%) of 2',4',6'-trichloro-3-N,N-dimethylaminocarbonylaminosulfonyl-4-nitrodiphenyl ether (Compound No. 26) as colorless powdery crystals of M.P. 186°–190° C.

(5) Synthesis of 2',4'-dibromo-3-methoxycarbonylaminosulfonyl-4-nitrodiphenyl ether (Compound No. 33)

To a solution of 2.3 g. (0.005 mole) of 2',4'-dibromo-3-aminosulfonyl-4-nitrodiphenyl ether in 80 ml. of acetone were added 1.1 g. (0.0075 mole) of potassium carbonate and further dropwise 0.7 g. (0.0075 mole) of methyl chloroformate with stirring. The resulting mixture was heated under reflux for 3 hours. Then, the reaction mixture was cooled, the inorganic salts thus separated were filtered off, the solvent was distilled off from the filtrate and then the residue was dissolved in a dilute aqueous solution of sodium hydroxide. Insoluble substances were filtered off and the filtrate was adjusted to pH 6.0 with the dropwise addition of a dilute aqueous solution of hydrochloric acid. The crystalline substance thus separated was recovered by filtration, dried and recrystallized from a mixture of benzene with n-hexane to give 1.1 g. (yield, 44%) of 2',4'-dibromo-3-methoxycarbonylaminosulfonyl-4-nitrodiphenyl ether (Compound No. 33) as pale yellow needles of M.P. 167°–172° C.

(6) Synthesis of 2',4'-dichloro-6'-fluoro-3-methoxycarbonylaminosulfonyl-4-nitrodiphenyl ether (Compound No. 38)

To a solution of 2.0 g. (0.005 mole) of 2',4'-dichloro-6'-fluoro-3-aminosulfonyl-4-nitrodiphenyl ether in 80 ml. of acetone were added 1.2 g. (0.008 mole) of potassium carbonate and 0.8 g. (0.008 mole) of methyl chloroformate and the resulting mixture was heated under reflux for 6 hours. After cooling, the inorganic salts thus separated were filtered off, the solvent was distilled off from the filtrate, the residue was dissolved in a dilute aqueous solution of sodium hydroxide. Then, insoluble substances were filtered off, the filtrate was adjusted to pH 6 with the dropwise addition of a dilute aqueous solution of hydrochloric acid and the so separated crystalline substance was filtered off. The filtrate was made acidic with a strong hydrochloric acid, the crystalline substance thus separated was recovered by filtration, dried and recrystallized from benzene to give 1.3 g. (yield, 57%) of 2',4'-dichloro-6'-fluoro-3-methoxycarbonylaminosulfornyl-4-nitrodiphenyl ether (Compound No. 38) as pale yellow prisms of M.P. 152°–156° C.

(7) Synthesis of 2'-chloro-4'-trifluoromethyl-3-methoxycarbonylaminosulfonyl-4-nitrodiphenyl ether (Compound No. 52)

To a solution of 2.2 g. (0.0055 mole) of 2'-chloro-4'-trifluoromethyl-3-aminosulfonyl-4-nitrodiphenyl ether in 50 ml. of acetone were added 1.1 g. (0.008 mole) of potassium carbonate and 0.7 g. (0.008 mole) of methyl chloroformate and the resulting mixture was heated under reflux for 3.5 hours. Then, the acetone was distilled off, to the residue were added 50 ml. of water and insolubles were filtered off. The filtrate was made strongly acidic with hydrochloric acid, the so separated crystalline substance was collected by filtration, dried and then recrystallized from a mixture of benzene with n-hexane to yield 2.1 g. (yield, 84%) of 2'-chloro-4'-trifluoromethyl-3-methoxycarbonylaminosulfornyl-4-nitrodiphenyl ether (Compound No. 52) as pale yellow prisms with M.P. 127°–130° C.

(8) Synthesis of 2'-chloro-4'-trifluoromethyl-3-acetylaminosulfonyl-4-nitrodiphenyl ether (Compound No. 61)

To a solution of 2.4 g. (0.006 mole) of 2'-chloro-4'-trifluoromethyl-3-aminosulfonyl-4-nitrodiphenyl ether in 60 ml. of acetone was added an acetone solution of 1.2 g. (0.009 mole) of potassium carbonate and 0.6 g. (0.008 mole) of acetyl chloride and the resulting mixture was heated under reflux for 8 hours. Then, the acetone was distilled off, to the residue was added a dilute aqueous solution of sodium hydroxide, insoluble substances were filtered off and the filtrate was made strongly acidic with hydrochloric acid. The so separated crystalline substance was collected by filtration, dried and then recrystallized from a mixture of benzene with n-hexane to afford 2.4 g. (yield, 91%) of 2'-chloro-4'-trifluoromethyl-3-acetylaminosulfonyl-4-nitrodiphenyl ether (Compound No. 61) as pale yellow prisms with M.P. 152°–155° C.

(9) Synthesis of 2'-bromo-4'-trifluoromethyl-3-N,N-dimethylcarbamoylaminosulfonyl-4-nitrodiphenyl ether (Compound No. 73)

To a solution of 1.5 g. (0.0034 mole) of 2'-bromo-4'-trifluoromethyl-3-aminosulfonyl-4-nitrodiphenyl ether in 60 ml. of acetone were added 0.6 g. (0.0044 mole) of potassium carbonate and 0.5 g. (0.0045 mole) of N,N-dimethylcarbamoyl chloride and the resulting mixture was heated under reflux for 8 hours. Thereafter, the reaction mixture was treated according to the procedures of Example 4, (8) to give 0.8 g. (yield, 46%) of 2'-bromo-4'-trifluoromethyl-3-N,N-dimethylcarbamoylaminosulfonyl-4-nitrodiphenyl ether (Compound No. 73) as colorless powders with M.P. 160°–162° C.

In another aspect of this invention, there is provided a herbicidal composition which comprises as an active ingredient the diphenyl ether derivative of the above formula (I) and an agriculturally acceptable carrier.

When the diphenyl ether derivative of this invention is to be applied as herbicides, the derivative may be formulated for use with preparations commonly employed in a herbicide composition, for example, dusts, granules, wettable powders, emulsifiable concentrates, water soluble powders, liquid formulations and so on, with admixture of an inert carrier and, if required, other auxiliary agents.

As the inert carrier, there may be mentioned any of solid, liquid or gaseous carriers ordinarily employed in the art for herbicides and, for example, talc, clay, kaolin, diatomaceous earth, calcium carbonate, bentonite, white carbon, benzene, xylene, n-hexane, methylnaphthalene, cyclohexanone, isophoron and the like.

The herbicidal composition of this invention may also optionally be blended with any auxiliary agents for preparation, for example, spreaders, diluents, surface active agents, solvents and the like as usually done in the art.

Moreover, the herbicidal composition of this invention may also be admixed with other herbicides, fungicides, insecticides, other agricultural chemicals, fertilizers, e.g., urea, ammonium sulfate, ammonium phosphate, potassic fertilizers, soil conditioners and the like. As the herbicides which may advantageously be admixed with the compound of formula (I), there may be mentioned a thiocarbamate type herbicide such as Benthiocarb (Saturn), Molinate (Ordram), etc., an acid amide type herbicide such as Alachlor (Rasso), Butachlor (Machete), etc.; a phenoxy type herbicide such as 2,4-PA, MCP, etc.; a diphenyl ether type herbicide such as Nitrofen (NIP), Chlornitrofen (MO), etc.; a urea type herbicide such as Diuron (Karmex D), Linuron (Afalon), etc.; a triazine type herbicide such as Simazin (Prinsep), Afrazin (Gesaprim), etc.; and other herbicides such as Triflurolin (Treflan), Oxadiazon (Ronstar), ACN (Mogeton), Bentaron (Basagran), etc.

The above-mentioned carriers and various auxiliary agents may be optionally utilized alone or in combination therewith for desired purposes.

In general, the herbicidal composition of this invention may contain the diphenyl ether derivative in an amount of 0.1–99% by weight, based upon the finished composition and the content of the active derivative in herbicidal composition may usually depend upon the preparation form to be formulated, for instance, ordinarily 1–25 parts by weight for dusts, 25–90 parts by weight for wettable powders, 1–35 parts by weight for granules, 5–50 parts by weight for emulsifiable concentrates and the like.

The amount of the herbicidal composition to be applied usually to a field is 1–100 g./are with respect to the active ingredient of this invention.

Examples of the preparation of the present herbicidal composition are given below. All parts are given by weight hereinafter unless otherwise stated.

EXAMPLE 5

Granules (1) 8 parts of 2′,3′-dichloro-3-aminosulfonyl-4-nitrodiphenyl ether (Compound No. 5), 30 parts of bentonite, 59 parts of talc, 1 part of "Neopelex powder" (trade name of surfactant from Kao-Atlas K.K.) and 2 parts of sodium lignosulfonate were homogeneously blended. To the blend was added a small amount of water and the mixture was kneaded, granulated and dried to give granules.

(2) 5 parts of 2′-chloro-4′-trifluoromethyl-3-acetylaminosulfonyl-4-nitrodiphenyl ether (Compound No. 61), 30 parts of bentonite, 60 parts of talc, 2 parts of sodium naphthalenesulfonate and 3 parts of sodium lignosulfonate were blended and pulverized. The mixture was kneaded with a proper amount of water and granulated by means of a granulating machine to give granules.

EXAMPLE 6

Wettable powders (1) 50 parts of 2′,4′-dichloro-3-methoxycarbonylaminosulfonyl-4-nitrodiphenyl ether (Compound No. 9), 48 parts of Kaolin and 2 parts of Neopelex powder were homogeneously blended and pulverized to give wettable powders.

(2) 50 parts of 2′-chloro-4′-trifluoromethyl-3-aminosulfonyl-4-nitrodiphenyl ether (Compound No. 51), 30 parts of Kaolin, 15 parts of bentonite and 5 parts of sodium lignosulfonate were mixed and pulverized to give wettable powders.

EXAMPLE 7

Emulsifiable concentrates (1) 50 parts of 2′,4′-dichloro-3-ethoxycarbonylaminosulfonyl-4-nitrodiphenyl ether (Compound No. 10), 40 parts of xylene, 5 parts of dimethylformamide and 5 part of "Toxanon" (trade name of surfactant from Sanyo Kasei Kogyo K.K.) were homogeneously blended and dissolved to give emulsifiable concentrates.

(2) 50 parts of 2′-chloro-4′-trifluoromethyl-3-methoxycarbonylaminosulfonyl-4-nitrodiphenyl ether (Compound No. 52), 30 parts of xylene, 10 parts of isophorone and 10 parts of an emulsifier "Solpol" (trade name) were blended and dissolved to give emulsifiable concentrates.

EXAMPLE 8

Dusts (1) 5 parts of 2′,4′,6′-trichloro-3-methoxycarbonylaminosulfonyl-4-nitrodiphenyl ether (Compound No. 23), 50 parts of talc and 45 parts of Kaolin were homogeneously blended to give dusts.

(2) 5 parts of 2′-chloro-4′-trifluoromethyl-3-N,N-dimethylcarbamoylaminosulfonyl-4-nitrodiphenyl ether (Compound No. 54), 50 parts of talc and 45 parts of Kaolin were homogeneously blended and pulverized to give dusts.

Experimental examples of the present herbicidal compositions are given below in order to illustrate herbicidal effects of the present composition more fully. In these Experiments, the test compounds' numbers are the same Compound Nos. as designated hereinabove and the test compounds are applied in the form of the wettable powder prepared according to the procedures of the above Example 6, which is used after dilution with water to a concentration of the active ingredient of 1000 ppm.

EXPERIMENT 1

Water surface application (soil treatment) tests for paddy field weed control (1) Wagner pots, each having a surface of 1/5000 are, were packed with Ube soil (alluvial soil) and transplanted with seeds of barnyardgrass, tubes of "Mizugayatsuri" (*Cyperus serotinus* Rottb.) and of "Urikawa"0 (*Sagittaria pymaea* Miq.) and stocks of slender spikerush. Then, the pots were slightly covered with soil and seeds of monochoria and of "Hotarui" (*Scirpus hotarui* Ohwi) were sowed thereover and rice plant seedlings at 2 leaf stage (variety: Nihonbare) were also transplanted. Then, the pots were filled with water to a depth of 3 cm.

At the date of germination of weeds, each test compound at the indicated dose was applied dropwise with a pipette and the pots were kept in a glass chamber at an average temperature of approximately 25° C.

After 3 weeks from the treatment, herbicidal effects of each test compound were investigated.

The results are summarized in the following Table 2 wherein herbicidal effects were evaluated according to the rating system as defined below:

TABLE 2

5 = Completely killed;   4 = Severely damaged;
3 = Moderately damaged;  2 = Slightly damaged;
1 = Minor damaged;       0 = None (normal development)

| Test compound No. | Dose g./are | Rice seedlings | Barnyardgrass | *Cyperus serotinus* | Slender spike rush | *Scirpus hotarui* | Monochoria | *Sagittaria pymaea* |
|---|---|---|---|---|---|---|---|---|
|    | 50   | 0 | 4 | 4 | 3 | 5 | 5 | 4 |
| 1  | 25   | 0 | 3 | 2 | 3 | 5 | 5 | 3 |
|    | 12.5 | 0 | 2 | 1 | 1 | 5 | 5 | 3 |
|    | 50   | 0 | 5 | 5 | 5 | 5 | 5 | 5 |
| 2  | 25   | 0 | 5 | 5 | 4 | 5 | 5 | 5 |
|    | 12.5 | 0 | 4 | 4 | 3 | 5 | 5 | 4 |
|    | 50   | 0 | 5 | 5 | 5 | 5 | 5 | 5 |
| 3  | 25   | 0 | 4 | 5 | 4 | 5 | 5 | 5 |
|    | 12.5 | 0 | 4 | 4 | 3 | 5 | 5 | 4 |
|    | 50   | 0 | 4 | 3 | 3 | 5 | 5 | 4 |
| 4  | 25   | 0 | 2 | 2 | 3 | 5 | 5 | 3 |
|    | 12.5 | 0 | 2 | 1 | 2 | 5 | 5 | 2 |
|    | 50   | 0 | 4 | 3 | 3 | 5 | 5 | 4 |
| 5  | 25   | 0 | 3 | 2 | 3 | 5 | 5 | 4 |
|    | 12.5 | 0 | 2 | 2 | 2 | 5 | 5 | 2 |
|    | 50   | 0 | 5 | 5 | 5 | 5 | 5 | 5 |
| 6  | 25   | 0 | 5 | 5 | 4 | 5 | 5 | 5 |
|    | 12.5 | 0 | 4 | 4 | 4 | 5 | 5 | 4 |
|    | 50   | 0 | 5 | 5 | 5 | 5 | 5 | 5 |
| 7  | 25   | 0 | 5 | 5 | 4 | 5 | 5 | 5 |
|    | 12.5 | 0 | 3 | 4 | 3 | 5 | 5 | 4 |
|    | 50   | 0 | 3 | 3 | 2 | 5 | 5 | 4 |
| 8  | 25   | 0 | 2 | 2 | 1 | 5 | 5 | 2 |
|    | 12.5 | 0 | 1 | 2 | 0 | 5 | 5 | 1 |
|    | 50   | 0 | 5 | 5 | 5 | 5 | 5 | 5 |
| 9  | 25   | 0 | 5 | 5 | 5 | 5 | 5 | 5 |
|    | 12.5 | 0 | 5 | 5 | 5 | 5 | 5 | 5 |
|    | 50   | 0 | 5 | 5 | 5 | 5 | 5 | 5 |
| 10 | 25   | 0 | 5 | 5 | 5 | 5 | 5 | 5 |
|    | 12.5 | 0 | 5 | 5 | 5 | 5 | 5 | 5 |
|    | 50   | 0 | 5 | 5 | 5 | 5 | 5 | 5 |
| 11 | 25   | 0 | 5 | 5 | 5 | 5 | 5 | 5 |
|    | 12.5 | 0 | 5 | 5 | 5 | 5 | 5 | 5 |
|    | 50   | 0 | 5 | 5 | 5 | 5 | 5 | 5 |
| 12 | 25   | 0 | 5 | 5 | 4 | 5 | 5 | 5 |
|    | 12.5 | 0 | 4 | 3 | 3 | 5 | 5 | 4 |
|    | 50   | 0 | 5 | 5 | 5 | 5 | 5 | 5 |
| 13 | 25   | 0 | 5 | 5 | 4 | 5 | 5 | 5 |
|    | 12.5 | 0 | 3 | 4 | 2 | 5 | 5 | 4 |
|    | 50   | 0 | 5 | 5 | 5 | 5 | 5 | 5 |
| 14 | 25   | 0 | 5 | 5 | 4 | 5 | 5 | 5 |
|    | 12.5 | 0 | 4 | 3 | 2 | 5 | 5 | 4 |
|    | 50   | 0 | 5 | 5 | 5 | 5 | 5 | 5 |
| 15 | 25   | 0 | 5 | 5 | 4 | 5 | 5 | 5 |
|    | 12.5 | 0 | 4 | 3 | 3 | 5 | 5 | 4 |
|    | 50   | 0 | 3 | 3 | 2 | 5 | 5 | 4 |
| 16 | 25   | 0 | 2 | 1 | 2 | 5 | 5 | 3 |
|    | 12.5 | 0 | 2 | 1 | 1 | 5 | 5 | 3 |
|    | 50   | 0 | 3 | 2 | 3 | 5 | 5 | 4 |
| 17 | 25   | 0 | 2 | 1 | 2 | 5 | 5 | 4 |
|    | 12.5 | 0 | 1 | 1 | 1 | 5 | 5 | 2 |
|    | 50   | 0 | 4 | 3 | 3 | 5 | 5 | 3 |
| 18 | 25   | 0 | 2 | 2 | 2 | 5 | 5 | 3 |
|    | 12.5 | 0 | 2 | 1 | 1 | 5 | 5 | 2 |
|    | 50   | 0 | 5 | 5 | 4 | 5 | 5 | 5 |
| 19 | 25   | 0 | 5 | 4 | 3 | 5 | 5 | 5 |
|    | 12.5 | 0 | 3 | 2 | 2 | 5 | 5 | 4 |
|    | 50   | 0 | 5 | 5 | 5 | 5 | 5 | 5 |
| 20 | 25   | 0 | 5 | 4 | 3 | 5 | 5 | 5 |
|    | 12.5 | 0 | 4 | 2 | 2 | 5 | 5 | 4 |
|    | 50   | 0 | 4 | 3 | 2 | 5 | 5 | 4 |
| 21 | 25   | 0 | 2 | 1 | 2 | 5 | 5 | 2 |
|    | 12.5 | 0 | 1 | 1 | 1 | 5 | 5 | 1 |
|    | 50   | 0 | 3 | 3 | 2 | 5 | 5 | 4 |
| 22 | 25   | 0 | 2 | 2 | 1 | 5 | 5 | 2 |
|    | 12.5 | 0 | 1 | 1 | 1 | 5 | 5 | 2 |
|    | 50   | 0 | 5 | 5 | 5 | 5 | 5 | 5 |
| 23 | 25   | 0 | 5 | 5 | 5 | 5 | 5 | 5 |
|    | 12.5 | 0 | 5 | 5 | 5 | 5 | 5 | 5 |
|    | 50   | 0 | 5 | 5 | 5 | 5 | 5 | 5 |
| 24 | 25   | 0 | 5 | 5 | 5 | 5 | 5 | 5 |
|    | 12.5 | 0 | 5 | 5 | 5 | 5 | 5 | 5 |
|    | 50   | 0 | 5 | 5 | 5 | 5 | 5 | 5 |
| 25 | 25   | 0 | 5 | 5 | 5 | 5 | 5 | 5 |

TABLE 2-continued

5 = Completely killed;  4 = Severely damaged;
3 = Moderately damaged;  2 = Slightly damaged;
1 = Minor damaged;  0 = None (normal development)

| Test compound No. | Dose g./are | Rice seedlings | Barnyard-grass | *Cyperus serotinus* | Slender spike rush | *Scirpus hotarui* | Monochoria | *Sagittaria pymaea* |
|---|---|---|---|---|---|---|---|---|
| | 12.5 | 0 | 5 | 5 | 5 | 5 | 5 | 5 |
| | 50 | 0 | 5 | 5 | 5 | 5 | 5 | 5 |
| 26 | 25 | 0 | 4 | 3 | 3 | 5 | 5 | 5 |
| | 12.5 | 0 | 3 | 3 | 2 | 5 | 5 | 4 |
| | 50 | 0 | 5 | 5 | 5 | 5 | 5 | 5 |
| 27 | 25 | 0 | 5 | 5 | 5 | 5 | 5 | 5 |
| | 12.5 | 0 | 5 | 5 | 5 | 5 | 5 | 5 |
| | 50 | 0 | 4 | 3 | 3 | 5 | 5 | 4 |
| 28 | 25 | 0 | 3 | 2 | 3 | 5 | 5 | 2 |
| | 12.5 | 0 | 3 | 1 | 1 | 5 | 5 | 1 |
| | 50 | 0 | 5 | 4 | 4 | 5 | 5 | 5 |
| 29 | 25 | 0 | 4 | 3 | 3 | 5 | 5 | 4 |
| | 12.5 | 0 | 3 | 2 | 2 | 5 | 5 | 3 |
| 30 | 50 | 0 | 5 | 4 | 5 | 5 | 5 | 5 |
| | 25 | 0 | 4 | 3 | 5 | 5 | 5 | 4 |
| | 12.5 | 0 | 3 | 2 | 2 | 5 | 5 | 3 |
| | 50 | 0 | 4 | 3 | 2 | 5 | 5 | 3 |
| 31 | 25 | 0 | 2 | 2 | 1 | 5 | 5 | 3 |
| | 12.5 | 0 | 2 | 1 | 1 | 5 | 5 | 2 |
| | 50 | 0 | 3 | 3 | 3 | 5 | 5 | 3 |
| 32 | 25 | 0 | 2 | 2 | 2 | 5 | 5 | 2 |
| | 12.5 | 0 | 2 | 1 | 2 | 5 | 5 | 1 |
| | 50 | 0 | 5 | 5 | 5 | 5 | 5 | 5 |
| 33 | 25 | 0 | 5 | 5 | 5 | 5 | 5 | 5 |
| | 12.5 | 0 | 5 | 5 | 5 | 5 | 5 | 5 |
| | 50 | 0 | 5 | 5 | 5 | 5 | 5 | 5 |
| 34 | 25 | 0 | 5 | 5 | 5 | 5 | 5 | 5 |
| | 12.5 | 0 | 5 | 5 | 5 | 5 | 5 | 5 |
| | 50 | 0 | 5 | 5 | 4 | 5 | 5 | 5 |
| 35 | 25 | 0 | 5 | 4 | 3 | 5 | 5 | 5 |
| | 12.5 | 0 | 3 | 3 | 2 | 5 | 5 | 4 |
| | 50 | 0 | 5 | 5 | 5 | 5 | 5 | 5 |
| 36 | 25 | 0 | 5 | 5 | 5 | 5 | 5 | 5 |
| | 12.5 | 0 | 5 | 5 | 5 | 5 | 5 | 5 |
| | 50 | 0 | 5 | 4 | 4 | 5 | 5 | 5 |
| 37 | 25 | 0 | 4 | 2 | 2 | 5 | 5 | 5 |
| | 12.5 | 0 | 4 | 2 | 2 | 5 | 5 | 4 |
| | 50 | 0 | 5 | 5 | 5 | 5 | 5 | 5 |
| 38 | 25 | 0 | 5 | 5 | 5 | 5 | 5 | 5 |
| | 12.5 | 0 | 5 | 5 | 5 | 5 | 5 | 5 |
| | 50 | 0 | 5 | 5 | 5 | 5 | 5 | 5 |
| 39 | 25 | 0 | 5 | 5 | 5 | 5 | 5 | 5 |
| | 12.5 | 0 | 5 | 5 | 5 | 5 | 5 | 5 |
| | 50 | 0 | 5 | 5 | 5 | 5 | 5 | 5 |
| 40 | 25 | 0 | 5 | 4 | 4 | 5 | 5 | 5 |
| | 12.5 | 0 | 4 | 3 | 4 | 5 | 5 | 4 |
| | 50 | 0 | 5 | 5 | 5 | 5 | 5 | 5 |
| 41 | 25 | 0 | 5 | 5 | 5 | 5 | 5 | 5 |
| | 12.5 | 0 | 4 | 3 | 4 | 5 | 5 | 5 |
| | 50 | 0 | 5 | 5 | 5 | 5 | 5 | 5 |
| 42 | 25 | 0 | 5 | 5 | 5 | 5 | 5 | 5 |
| | 12.5 | 0 | 4 | 4 | 3 | 5 | 5 | 4 |
| | 50 | 0 | 5 | 5 | 5 | 5 | 5 | 5 |
| 43 | 25 | 0 | 5 | 5 | 5 | 5 | 5 | 5 |
| | 12.5 | 0 | 5 | 4 | 4 | 5 | 5 | 4 |
| | 50 | 0 | 4 | 3 | 4 | 5 | 5 | 5 |
| 44 | 25 | 0 | 3 | 2 | 2 | 5 | 5 | 5 |
| | 12.5 | 0 | 2 | 1 | 2 | 4 | 5 | 4 |
| | 50 | 0 | 5 | 5 | 4 | 5 | 5 | 5 |
| 45 | 25 | 0 | 4 | 4 | 3 | 5 | 5 | 5 |
| | 12.5 | 0 | 4 | 2 | 3 | 5 | 5 | 4 |
| | 50 | 0 | 4 | 4 | 4 | 5 | 5 | 4 |
| 46 | 25 | 0 | 2 | 2 | 3 | 5 | 5 | 2 |
| | 12.5 | 0 | 2 | 1 | 2 | 4 | 5 | 2 |
| | 50 | 0 | 5 | 5 | 5 | 5 | 5 | 5 |
| 47 | 25 | 0 | 5 | 5 | 5 | 5 | 5 | 5 |
| | 12.5 | 0 | 5 | 4 | 5 | 5 | 5 | 4 |
| | 50 | 0 | 5 | 5 | 5 | 5 | 5 | 5 |
| 48 | 25 | 0 | 5 | 4 | 5 | 5 | 5 | 5 |
| | 12.5 | 0 | 4 | 4 | 4 | 4 | 5 | 3 |
| | 50 | 0 | 5 | 5 | 5 | 5 | 5 | 3 |
| 49 | 25 | 0 | 3 | 2 | 4 | 5 | 5 | 2 |
| | 12.5 | 0 | 2 | 2 | 2 | 3 | 4 | 1 |
| | 50 | 0 | 5 | 5 | 5 | 5 | 5 | 5 |
| 50 | 25 | 0 | 5 | 4 | 5 | 5 | 5 | 4 |
| | 12.5 | 0 | 4 | 3 | 3 | 4 | 5 | 3 |
| | 50 | 0 | 4 | 3 | 4 | 5 | 5 | 4 |

TABLE 2-continued

5 = Completely killed;    4 = Severely damaged;
3 = Moderately damaged;    2 = Slightly damaged;
1 = Minor damaged;    0 = None (normal development)

| Test compound No. | Dose g./are | Rice seedlings | Barnyardgrass | *Cyperus serotinus* | Slender spike rush | *Scirpus hotarui* | Monochoria | *Sagittaria pymaea* |
|---|---|---|---|---|---|---|---|---|
| 51 | 25 | 0 | 3 | 3 | 3 | 5 | 5 | 3 |
|  | 12.5 | 0 | 2 | 2 | 2 | 5 | 4 | 2 |
|  | 50 | 0 | 5 | 5 | 5 | 5 | 5 | 5 |
| 52 | 25 | 0 | 5 | 5 | 5 | 5 | 5 | 5 |
|  | 12.5 | 0 | 5 | 5 | 5 | 5 | 5 | 5 |
|  | 50 | 0 | 5 | 5 | 5 | 5 | 5 | 5 |
| 53 | 25 | 0 | 5 | 5 | 5 | 5 | 5 | 5 |
|  | 12.5 | 0 | 5 | 5 | 5 | 5 | 5 | 5 |
|  | 50 | 0 | 5 | 5 | 5 | 5 | 5 | 5 |
| 54 | 25 | 0 | 4 | 5 | 4 | 5 | 5 | 5 |
|  | 12.5 | 0 | 3 | 4 | 3 | 5 | 5 | 4 |
|  | 50 | 0 | 5 | 5 | 5 | 5 | 5 | 5 |
| NIP* | 25 | 0 | 5 | 4 | 4 | 5 | 5 | 2 |
|  | 12.5 | 0 | 5 | 2 | 4 | 4 | 5 | 0 |

*2',4'-Dichloro-4-nitro-diphenyl ether (2) Wagner pots, each having a surface of 1/5000 are, were packed with paddy field soil, transplanted in the surface thereof with weed seeds of barnyardgrass, false pimpernel, toothcup, smallflower umbrellaplant, "Hotarui" (*Scirpus hotarui* Ohwi) and "Heraomodaka" (*Alisma canaliculatum* A. Br. et Bouché), added with water and then plowed. Then, grown stocks of slender spikerush and tubers of "Urikawa" (*Sagittaria pymaea* Miq.) and "Mizugayatsuri" (*Cyperus serotinus* Rottb.) were planted and rice plant seedings at 4 or 5 leaf stage were transplanted. Then, the pots were filled with water to a depth of 3 cm. After 3 days, the test compounds were uniformly sprayed over the water surfaces of each pot at the indicated dose. The pots were kept for growth control in a glass chamber at 25° C. After 3 weeks from the treatment, herbicidal effect of each test compound was investigated.

The results are summarized in the following Table 3. Herbicidal effects were evaluated with the ratings as defined in Experiment 1, (1).

Table 3

| Test compound No. | Active ingredient amount g./are | Phytotoxicity to rice plants | Annual weed | | | | Perennial weed | | | | |
|---|---|---|---|---|---|---|---|---|---|---|---|
| | | | barnyardgrass | false pimpernel | toothcup | smallflower umbrellaplant | Hotarui | slender spikerush | Mizugayatsuri | Heraomodaka | Urikawa |
| 55 | 40 | 0 | 5 | 5 | 5 | 5 | 5 | 2 | 3 | 5 | 5 |
|  | 20 | 0 | 5 | 5 | 5 | 5 | 4 | 2 | 2 | 4 | 5 |
|  | 10 | 0 | 5 | 5 | 5 | 5 | 4 | 2 | 1 | 4 | 5 |
| 56 | 40 | 1 | 5 | 5 | 5 | 5 | 5 | 4 | 5 | 5 | 5 |
|  | 20 | 0 | 5 | 5 | 5 | 5 | 4 | 3 | 4 | 5 | 5 |
|  | 10 | 0 | 4 | 5 | 5 | 5 | 3 | 3 | 1 | 3 | 3 |
| 57 | 40 | 0 | 5 | 5 | 5 | 5 | 5 | 4 | 5 | 5 | 5 |
|  | 20 | 0 | 5 | 5 | 5 | 5 | 4 | 3 | 4 | 4 | 3 |
|  | 10 | 0 | 4 | 5 | 5 | 5 | 2 | 1 | 1 | 3 | 2 |
| 58 | 40 | 0 | 5 | 5 | 5 | 5 | 5 | 4 | 4 | 5 | 5 |
|  | 20 | 0 | 5 | 5 | 5 | 5 | 4 | 3 | 3 | 4 | 4 |
|  | 10 | 0 | 3 | 5 | 5 | 5 | 3 | 2 | 2 | 2 | 3 |
| 59 | 40 | 0 | 5 | 5 | 5 | 5 | 5 | 4 | 4 | 5 | 5 |
|  | 20 | 0 | 5 | 5 | 5 | 5 | 4 | 3 | 3 | 4 | 4 |
|  | 10 | 0 | 3 | 5 | 5 | 5 | 1 | 2 | 1 | 2 | 3 |
| 60 | 40 | 0 | 5 | 5 | 5 | 5 | 5 | 4 | 4 | 5 | 5 |
|  | 20 | 0 | 5 | 5 | 5 | 5 | 4 | 3 | 3 | 4 | 4 |
|  | 10 | 0 | 4 | 5 | 5 | 5 | 4 | 3 | 2 | 3 | 4 |
| 61 | 40 | 3 | 5 | 5 | 5 | 5 | 5 | 5 | 5 | 5 | 5 |
|  | 20 | 2 | 4 | 5 | 5 | 5 | 3 | 3 | 5 | 5 | 3 |
|  | 10 | 1 | 3 | 5 | 5 | 5 | 2 | 2 | 3 | 2 | 2 |
| 62 | 40 | 1 | 4 | 5 | 5 | 5 | 3 | 3 | 3 | 5 | 3 |
|  | 20 | 0 | 3 | 5 | 5 | 5 | 2 | 2 | 2 | 4 | 2 |
|  | 10 | 0 | 2 | 5 | 5 | 5 | 1 | 1 | 1 | 3 | 1 |
| 63 | 40 | 0 | 5 | 5 | 5 | 5 | 4 | 4 | 5 | 5 | 5 |
|  | 20 | 0 | 4 | 5 | 5 | 5 | 3 | 3 | 4 | 5 | 4 |
|  | 10 | 0 | 3 | 5 | 5 | 5 | 3 | 2 | 4 | 4 | 3 |
| 64 | 40 | 0 | 4 | 5 | 5 | 5 | 4 | 4 | 5 | 5 | 4 |
|  | 20 | 0 | 3 | 5 | 5 | 5 | 2 | 2 | 5 | 4 | 3 |
|  | 10 | 0 | 3 | 5 | 5 | 5 | 2 | 1 | 5 | 2 | 1 |
| 65 | 40 | 1 | 5 | 5 | 5 | 5 | 5 | 4 | 5 | 5 | 5 |
|  | 20 | 1 | 5 | 5 | 5 | 5 | 4 | 3 | 5 | 5 | 4 |
|  | 10 | 0 | 4 | 5 | 5 | 5 | 3 | 3 | 4 | 4 | 3 |
|  | 40 | 1 | 5 | 5 | 5 | 5 | 5 | 5 | 5 | 5 | 5 |

Table 3-continued

| Test compound No. | Active ingredient amount g./are | Phyto- toxicity to rice plants | Annual weed ||||  Perennial weed |||||
|---|---|---|---|---|---|---|---|---|---|---|---|
| | | | barn- yard- grass | false pim- per- nel | tooth cup | small- flower umbrella- plant | Hotarui | slender spike- rush | Mizu- gaya- tsuri | Herao- mo- daka | Uri- kawa |
| 66 | 20 | 1 | 5 | 5 | 5 | 5 | 4 | 4 | 5 | 5 | 5 |
| | 10 | 0 | 4 | 5 | 5 | 5 | 3 | 3 | 5 | 5 | 4 |
| | 40 | 1 | 5 | 5 | 5 | 5 | 5 | 4 | 5 | 5 | 4 |
| 67 | 20 | 0 | 4 | 5 | 5 | 5 | 4 | 3 | 5 | 5 | 3 |
| | 10 | 0 | 3 | 5 | 5 | 5 | 3 | 2 | 5 | 4 | 3 |
| | 40 | 0 | 5 | 5 | 5 | 5 | 5 | 4 | 5 | 5 | 4 |
| 68 | 20 | 0 | 4 | 5 | 5 | 5 | 4 | 3 | 4 | 4 | 3 |
| | 10 | 0 | 3 | 5 | 5 | 5 | 2 | 2 | 3 | 3 | 1 |
| | 40 | 0 | 4 | 5 | 5 | 5 | 4 | 4 | 5 | 5 | 4 |
| 69 | 20 | 0 | 3 | 5 | 5 | 5 | 3 | 3 | 4 | 4 | 2 |
| | 10 | 0 | 3 | 5 | 5 | 5 | 2 | 1 | 3 | 3 | 1 |
| | 40 | 1 | 5 | 5 | 5 | 5 | 5 | 4 | 5 | 5 | 5 |
| 70 | 20 | 0 | 4 | 5 | 5 | 5 | 4 | 3 | 5 | 5 | 4 |
| | 10 | 0 | 3 | 5 | 5 | 5 | 3 | 2 | 5 | 5 | 3 |
| | 40 | 1 | 4 | 5 | 5 | 5 | 5 | 4 | 5 | 5 | 5 |
| 71 | 20 | 0 | 3 | 5 | 5 | 5 | 3 | 3 | 5 | 5 | 4 |
| | 10 | 0 | 1 | 5 | 5 | 5 | 2 | 1 | 5 | 5 | 3 |
| | 40 | 0 | 4 | 5 | 5 | 5 | 4 | 4 | 5 | 5 | 4 |
| 72 | 20 | 0 | 2 | 5 | 5 | 5 | 2 | 2 | 5 | 5 | 3 |
| | 10 | 0 | 1 | 5 | 5 | 5 | 2 | 2 | 4 | 4 | 1 |
| | 40 | 0 | 4 | 5 | 5 | 5 | 4 | 4 | 5 | 5 | 4 |
| 73 | 20 | 0 | 3 | 5 | 5 | 5 | 3 | 3 | 4 | 4 | 3 |
| | 10 | 0 | 2 | 5 | 5 | 5 | 2 | 1 | 3 | 3 | 1 |
| | 40 | 1 | 5 | 5 | 5 | 5 | 5 | 5 | 5 | 5 | 4 |
| 74 | 20 | 0 | 4 | 5 | 5 | 5 | 4 | 3 | 5 | 5 | 3 |
| | 10 | 0 | 3 | 5 | 5 | 5 | 3 | 2 | 5 | 4 | 2 |
| | 40 | 1 | 5 | 5 | 5 | 5 | 5 | 4 | 5 | 5 | 5 |
| 75 | 20 | 0 | 4 | 5 | 5 | 5 | 4 | 3 | 5 | 5 | 4 |
| | 10 | 0 | 3 | 5 | 5 | 5 | 3 | 2 | 5 | 5 | 3 |

EXPERIMENT 2

Tests against perennial weeds at various growth stages

Wagner pots, each having a surface of 1/5000 are, were packed with Ube soil and tubers of "Mizugayatsuri (*Cyperus serotinus* Rottb.)" and of "Urikawa (*Sagittaria pymaea* Miq.)" were planted and then the pots were filled with water to a depth of 3 cm.

Before germination and at the dates of grown heights of 5 cm. and 10 cm. in *Cyperus serotinus* and before germination and at 2 and 4 leaf stages in *Sagittaria pymaea*, each test compound at the indicated dose was applied dropwise with a pipette. Then, the pots were kept in a glass chamber at an average temperature of approximately 25° C.

After 2 weeks from the treatment, herbicidal effects of each test compound were investigated.

The results are summarized in Table 4 wherein the same rating systems as in the Experiment 1, (1) were applied.

Table 4

| Test compound No. | Dose g./are | Cyperus serotinus |||  Sagittaria pymaea |||
|---|---|---|---|---|---|---|---|
| | | Treatment ||||||
| | | Before germ. | 5 cm | 10 cm | Before germ. | 2 leaf stage | 4 leaf stage |
| | 40 | 5 | 5 | 5 | 5 | 5 | 5 |
| 9 | 20 | 5 | 5 | 5 | 5 | 5 | 4 |
| | 10 | 5 | 5 | 4 | 5 | 5 | 3 |
| | 40 | 5 | 5 | 5 | 5 | 5 | 5 |
| 10 | 20 | 5 | 5 | 5 | 5 | 5 | 5 |
| | 10 | 5 | 5 | 5 | 5 | 5 | 5 |
| | 40 | 5 | 5 | 4 | 5 | 5 | 2 |
| 11 | 20 | 5 | 5 | 3 | 5 | 5 | 1 |
| | 10 | 5 | 5 | 2 | 5 | 5 | 1 |
| | 40 | 5 | 5 | 4 | 5 | 5 | 5 |
| 23 | 20 | 5 | 5 | 3 | 5 | 5 | 5 |
| | 10 | 5 | 4 | 2 | 5 | 5 | 4 |
| | 40 | 5 | 5 | 4 | 5 | 5 | 5 |
| 24 | 20 | 5 | 4 | 2 | 5 | 5 | 4 |
| | 10 | 5 | 4 | 2 | 5 | 5 | 3 |
| | 40 | 5 | 5 | 4 | 5 | 5 | 5 |
| 25 | 20 | 5 | 5 | 3 | 5 | 5 | 5 |
| | 10 | 5 | 4 | 2 | 5 | 5 | 4 |
| | 40 | 5 | 5 | 4 | 5 | 5 | 5 |
| 27 | 20 | 5 | 4 | 2 | 5 | 5 | 4 |
| | 10 | 5 | 3 | 2 | 5 | 5 | 2 |
| | 40 | 5 | 4 | 2 | 5 | 5 | 1 |
| 33 | 20 | 5 | 2 | 1 | 5 | 4 | 0 |
| | 10 | 5 | 1 | 0 | 5 | 2 | 0 |
| | 40 | 5 | 5 | 5 | 5 | 5 | 5 |
| 52 | 20 | 5 | 5 | 5 | 5 | 5 | 4 |
| | 10 | 5 | 5 | 4 | 5 | 5 | 3 |
| | 40 | 5 | 5 | 5 | 5 | 5 | 5 |
| 53 | 20 | 5 | 5 | 4 | 5 | 5 | 4 |
| | 10 | 5 | 5 | 3 | 5 | 5 | 2 |
| | 40 | 5 | 2 | 0 | 5 | 2 | 0 |
| NIP | 20 | 3 | 0 | 0 | 1 | 0 | 0 |
| | 10 | 0 | 0 | 0 | 0 | 0 | 0 |

EXPERIMENT 3

Soil treatment tests for upland weed control (1) Wagner pots, each having a surface of 1/5000 are, were packed with Ube soil and then seeds of wheat (variety: Kobushikomugi), of soybean (variety: Natsudaizu No. 1) of mannagrass, of barnyardgrass, of common purslane, of pearlwort and of wavy bittercress were sowed. After covering with soil, each test compound was sprayed under pressure onto the soil surface at the indicated dose and then the pots were kept in a glass chamber at an average temperature of approximately 25° C.

After 2 weeks from the treatment, herbicidal effects of each test compound were investigated.

The results are summarized in Table 5 wherein the same rating system as in the Experiment 1, (1) were applied.

Table 5

| Test compound No. | Dose g./are | Wheat | Soy-bean | Manna-grass | Barn-yard-grass | Common purs-lane | Pearl-wort | Wavy bitter-cress |
|---|---|---|---|---|---|---|---|---|
| 1 | 50 | 0 | 0 | 3 | 5 | 4 | 4 | 5 |
|   | 25 | 0 | 0 | 2 | 4 | 3 | 2 | 3 |
|   | 12.5 | 0 | 0 | 1 | 4 | 3 | 0 | 3 |
| 2 | 50 | 0 | 0 | 4 | 5 | 5 | 5 | 5 |
|   | 25 | 0 | 0 | 3 | 5 | 5 | 5 | 5 |
|   | 12.5 | 0 | 0 | 2 | 5 | 5 | 5 | 5 |
| 3 | 50 | 0 | 0 | 4 | 5 | 5 | 5 | 5 |
|   | 25 | 0 | 0 | 4 | 5 | 5 | 5 | 5 |
|   | 12.5 | 0 | 0 | 3 | 5 | 5 | 5 | 5 |
| 4 | 50 | 0 | 0 | 3 | 5 | 5 | 5 | 5 |
|   | 25 | 0 | 0 | 2 | 5 | 5 | 5 | 5 |
|   | 12.5 | 0 | 0 | 1 | 5 | 5 | 5 | 5 |
| 5 | 50 | 0 | 0 | 3 | 4 | 5 | 3 | 5 |
|   | 25 | 0 | 0 | 2 | 4 | 2 | 1 | 3 |
|   | 12.5 | 0 | 0 | 1 | 4 | 2 | 0 | 2 |
| 6 | 50 | 0 | 0 | 4 | 5 | 5 | 5 | 5 |
|   | 25 | 0 | 0 | 3 | 5 | 5 | 5 | 5 |
|   | 12.5 | 0 | 0 | 3 | 5 | 5 | 5 | 5 |
| 7 | 50 | 0 | 0 | 4 | 5 | 5 | 5 | 5 |
|   | 25 | 0 | 0 | 3 | 5 | 5 | 5 | 5 |
|   | 12.5 | 0 | 0 | 2 | 5 | 5 | 5 | 5 |
| 8 | 50 | 0 | 0 | 3 | 5 | 5 | 2 | 3 |
|   | 25 | 0 | 0 | 1 | 4 | 4 | 1 | 2 |
|   | 12.5 | 0 | 0 | 0 | 3 | 3 | 0 | 1 |
| 9 | 50 | 0 | 0 | 5 | 5 | 5 | 5 | 5 |
|   | 25 | 0 | 0 | 4 | 5 | 5 | 5 | 5 |
|   | 12.5 | 0 | 0 | 4 | 5 | 5 | 5 | 5 |
| 10 | 50 | 0 | 0 | 5 | 5 | 5 | 5 | 5 |
|   | 25 | 0 | 0 | 4 | 5 | 5 | 5 | 5 |
|   | 12.5 | 0 | 0 | 4 | 5 | 5 | 5 | 5 |
| 11 | 50 | 0 | 0 | 4 | 5 | 5 | 5 | 5 |
|   | 25 | 0 | 0 | 3 | 5 | 5 | 5 | 5 |
|   | 12.5 | 0 | 0 | 3 | 5 | 5 | 5 | 5 |
| 12 | 50 | 0 | 0 | 4 | 5 | 5 | 5 | 5 |
|   | 25 | 0 | 0 | 3 | 5 | 5 | 5 | 5 |
|   | 12.5 | 0 | 0 | 2 | 5 | 5 | 5 | 5 |
| 13 | 50 | 0 | 0 | 4 | 5 | 5 | 5 | 5 |
|   | 25 | 0 | 0 | 3 | 5 | 5 | 5 | 5 |
|   | 12.5 | 0 | 0 | 2 | 5 | 5 | 5 | 5 |
| 14 | 50 | 0 | 0 | 4 | 5 | 5 | 5 | 5 |
|   | 25 | 0 | 0 | 3 | 5 | 5 | 5 | 5 |
|   | 12.5 | 0 | 0 | 2 | 5 | 5 | 5 | 5 |
| 15 | 50 | 0 | 0 | 3 | 5 | 5 | 5 | 5 |
|   | 25 | 0 | 0 | 3 | 5 | 5 | 5 | 5 |
|   | 12.5 | 0 | 0 | 2 | 5 | 5 | 5 | 5 |
| 16 | 50 | 0 | 0 | 3 | 4 | 5 | 2 | 5 |
|   | 25 | 0 | 0 | 2 | 4 | 4 | 1 | 4 |
|   | 12.5 | 0 | 0 | 1 | 4 | 4 | 0 | 3 |
| 17 | 50 | 0 | 0 | 3 | 5 | 5 | 3 | 5 |
|   | 25 | 0 | 0 | 2 | 4 | 4 | 2 | 4 |
|   | 12.5 | 0 | 0 | 2 | 3 | 3 | 0 | 4 |
| 18 | 50 | 0 | 0 | 3 | 4 | 5 | 2 | 4 |
|   | 25 | 0 | 0 | 2 | 4 | 4 | 1 | 3 |
|   | 12.5 | 0 | 0 | 1 | 4 | 3 | 0 | 3 |
| 19 | 50 | 0 | 0 | 3 | 5 | 5 | 5 | 5 |
|   | 25 | 0 | 0 | 2 | 5 | 5 | 5 | 5 |
|   | 12.5 | 0 | 0 | 1 | 5 | 5 | 5 | 5 |
| 20 | 50 | 0 | 0 | 4 | 5 | 5 | 5 | 5 |
|   | 25 | 0 | 0 | 3 | 5 | 5 | 5 | 5 |
|   | 12.5 | 0 | 0 | 3 | 5 | 5 | 5 | 5 |
| 21 | 50 | 0 | 0 | 2 | 5 | 5 | 5 | 5 |
|   | 25 | 0 | 0 | 1 | 5 | 5 | 5 | 5 |
|   | 12.5 | 0 | 0 | 0 | 5 | 5 | 5 | 5 |
| 22 | 50 | 0 | 0 | 3 | 5 | 5 | 3 | 4 |
|   | 25 | 0 | 0 | 1 | 4 | 5 | 2 | 3 |
|   | 12.5 | 0 | 0 | 0 | 4 | 4 | 0 | 3 |
| 23 | 50 | 0 | 0 | 5 | 5 | 5 | 5 | 5 |
|   | 25 | 0 | 0 | 5 | 5 | 5 | 5 | 5 |
|   | 12.5 | 0 | 0 | 5 | 5 | 5 | 5 | 5 |
| 24 | 50 | 0 | 0 | 5 | 5 | 5 | 5 | 5 |
|   | 25 | 0 | 0 | 5 | 5 | 5 | 5 | 5 |
|   | 12.5 | 0 | 0 | 5 | 5 | 5 | 5 | 5 |

Table 5-continued

| Test compound No. | Dose g./are | Wheat | Soy-bean | Manna-grass | Barn-yard-grass | Common purs-lane | Pearl-wort | Wavy bitter-cress |
|---|---|---|---|---|---|---|---|---|
| | 50 | 0 | 0 | 5 | 5 | 5 | 5 | 5 |
| 25 | 25 | 0 | 0 | 5 | 5 | 5 | 5 | 5 |
| | 12.5 | 0 | 0 | 5 | 5 | 5 | 5 | 5 |
| | 50 | 0 | 0 | 4 | 5 | 5 | 5 | 5 |
| 26 | 25 | 0 | 0 | 3 | 5 | 5 | 5 | 5 |
| | 12.5 | 0 | 0 | 3 | 5 | 5 | 5 | 5 |
| | 50 | 0 | 0 | 5 | 5 | 5 | 5 | 5 |
| 27 | 25 | 0 | 0 | 5 | 5 | 5 | 5 | 5 |
| | 12.5 | 0 | 0 | 5 | 5 | 5 | 5 | 5 |
| | 50 | 0 | 0 | 3 | 5 | 4 | 2 | 5 |
| 28 | 25 | 0 | 0 | 2 | 4 | 3 | 1 | 4 |
| | 12.5 | 0 | 0 | 1 | 3 | 3 | 0 | 3 |
| | 50 | 0 | 0 | 4 | 5 | 5 | 5 | 5 |
| 29 | 25 | 0 | 0 | 3 | 5 | 5 | 5 | 5 |
| | 12.5 | 0 | 0 | 3 | 5 | 5 | 5 | 5 |
| | 50 | 0 | 0 | 4 | 5 | 5 | 5 | 5 |
| 30 | 25 | 0 | 0 | 3 | 5 | 5 | 5 | 5 |
| | 12.5 | 0 | 0 | 2 | 5 | 5 | 5 | 5 |
| | 50 | 0 | 0 | 2 | 5 | 5 | 5 | 5 |
| 31 | 25 | 0 | 0 | 1 | 5 | 5 | 5 | 5 |
| | 12.5 | 0 | 0 | 0 | 5 | 5 | 5 | 5 |
| | 50 | 0 | 0 | 2 | 5 | 4 | 2 | 5 |
| 32 | 25 | 0 | 0 | 1 | 4 | 3 | 1 | 3 |
| | 12.5 | 0 | 0 | 0 | 4 | 2 | 0 | 3 |
| | 50 | 0 | 0 | 5 | 5 | 5 | 5 | 5 |
| 33 | 25 | 0 | 0 | 4 | 5 | 5 | 5 | 5 |
| | 12.5 | 0 | 0 | 4 | 5 | 5 | 5 | 5 |
| | 50 | 0 | 0 | 5 | 5 | 5 | 5 | 5 |
| 34 | 25 | 0 | 0 | 4 | 5 | 5 | 5 | 5 |
| | 12.5 | 0 | 0 | 3 | 5 | 5 | 5 | 5 |
| | 50 | 0 | 0 | 4 | 5 | 5 | 5 | 5 |
| 35 | 25 | 0 | 0 | 3 | 5 | 5 | 5 | 5 |
| | 12.5 | 0 | 0 | 3 | 5 | 5 | 5 | 5 |
| | 50 | 0 | 0 | 5 | 5 | 5 | 5 | 5 |
| 36 | 25 | 0 | 0 | 5 | 5 | 5 | 5 | 5 |
| | 12.5 | 0 | 0 | 4 | 5 | 5 | 5 | 5 |
| | 50 | 0 | 0 | 5 | 5 | 5 | 5 | 5 |
| 37 | 25 | 0 | 0 | 4 | 5 | 5 | 5 | 5 |
| | 12.5 | 0 | 0 | 2 | 4 | 4 | 3 | 5 |
| | 50 | 0 | 0 | 5 | 5 | 5 | 5 | 5 |
| 38 | 25 | 0 | 0 | 5 | 5 | 5 | 5 | 5 |
| | 12.5 | 0 | 0 | 5 | 5 | 5 | 5 | 5 |
| | 50 | 0 | 0 | 5 | 5 | 5 | 5 | 5 |
| 39 | 25 | 0 | 0 | 5 | 5 | 5 | 5 | 5 |
| | 12.5 | 0 | 0 | 5 | 5 | 5 | 5 | 5 |
| | 50 | 0 | 0 | 5 | 5 | 5 | 5 | 5 |
| 40 | 25 | 0 | 0 | 5 | 5 | 5 | 5 | 5 |
| | 12.5 | 0 | 0 | 4 | 5 | 5 | 4 | 4 |
| | 50 | 0 | 0 | 5 | 5 | 5 | 5 | 5 |
| 41 | 25 | 0 | 0 | 5 | 5 | 5 | 5 | 5 |
| | 12.5 | 0 | 0 | 5 | 5 | 5 | 5 | 5 |
| | 50 | 0 | 0 | 5 | 5 | 5 | 5 | 5 |
| 42 | 25 | 0 | 0 | 5 | 5 | 5 | 5 | 5 |
| | 12.5 | 0 | 0 | 4 | 5 | 5 | 5 | 5 |
| | 50 | 0 | 0 | 5 | 5 | 5 | 5 | 5 |
| 43 | 25 | 0 | 0 | 5 | 5 | 5 | 5 | 5 |
| | 12.5 | 0 | 0 | 5 | 5 | 5 | 5 | 5 |
| | 50 | 0 | 0 | 3 | 5 | 5 | 5 | 5 |
| 44 | 25 | 0 | 0 | 2 | 5 | 4 | 4 | 3 |
| | 12.5 | 0 | 0 | 1 | 3 | 2 | 2 | 2 |
| | 50 | 0 | 0 | 5 | 5 | 5 | 5 | 5 |
| 45 | 25 | 0 | 0 | 4 | 5 | 5 | 4 | 4 |
| | 12.5 | 0 | 0 | 3 | 4 | 4 | 3 | 3 |
| | 50 | 0 | 0 | 4 | 4 | 5 | 5 | 5 |
| 46 | 25 | 0 | 0 | 2 | 4 | 4 | 4 | 3 |
| | 12.5 | 0 | 0 | 1 | 2 | 2 | 3 | 2 |
| | 50 | 0 | 0 | 5 | 5 | 5 | 5 | 5 |
| 47 | 25 | 0 | 0 | 5 | 5 | 5 | 5 | 5 |
| | 12.5 | 0 | 0 | 4 | 4 | 5 | 4 | 4 |
| | 50 | 0 | 0 | 5 | 5 | 5 | 5 | 5 |
| 48 | 25 | 0 | 0 | 4 | 5 | 5 | 4 | 5 |
| | 12.5 | 0 | 0 | 3 | 3 | 4 | 3 | 3 |
| | 50 | 0 | 0 | 5 | 5 | 5 | 5 | 5 |
| 49 | 25 | 0 | 0 | 4 | 4 | 5 | 4 | 4 |
| | 12.5 | 0 | 0 | 2 | 2 | 3 | 2 | 2 |
| | 50 | 0 | 0 | 5 | 5 | 5 | 5 | 5 |
| 50 | 25 | 0 | 0 | 5 | 5 | 5 | 5 | 5 |
| | 12.5 | 0 | 0 | 4 | 4 | 4 | 3 | 4 |

Table 5-continued

| Test compound No. | Dose g./are | Wheat | Soy-bean | Manna-grass | Barn-yard-grass | Common purs-lane | Pearl-wort | Wavy bitter-cress |
|---|---|---|---|---|---|---|---|---|
|  | 50 | 0 | 0 | 3 | 4 | 4 | 4 | 5 |
| 51 | 25 | 0 | 0 | 2 | 3 | 4 | 3 | 4 |
|  | 12.5 | 0 | 0 | 1 | 2 | 3 | 1 | 4 |
|  | 50 | 0 | 0 | 4 | 5 | 5 | 5 | 5 |
| 52 | 25 | 0 | 0 | 3 | 4 | 5 | 5 | 5 |
|  | 12.5 | 0 | 0 | 2 | 4 | 5 | 5 | 5 |
|  | 50 | 0 | 0 | 4 | 5 | 5 | 5 | 5 |
| 53 | 25 | 0 | 0 | 3 | 5 | 5 | 5 | 5 |
|  | 12.5 | 0 | 0 | 2 | 4 | 5 | 5 | 5 |
|  | 50 | 0 | 0 | 3 | 4 | 5 | 5 | 5 |
| 54 | 25 | 0 | 0 | 2 | 3 | 5 | 5 | 5 |
|  | 12.5 | 0 | 0 | 1 | 2 | 4 | 5 | 5 |
|  | 50 | 0 | 0 | 5 | 5 | 5 | 0 | 5 |
| NIP | 25 | 0 | 0 | 5 | 5 | 5 | 0 | 5 |
|  | 12.5 | 0 | 0 | 5 | 4 | 4 | 0 | 3 |

(2) Wagner pots, each having a surface of 1/5000 are, were packed with upland soil and then sowed with seeds of wheat, maiz, soybean and cotton. The pots were covered with soil, in which weed seeds of mannagrass, common purslane, white goose-foot, wild amaranth and chufa were previously blended, and then watered. After 1 day, the test compounds were applied by spraying to the soil surface at the indicated dose. The pots were kept for growth control in a glass chamber at 25° C. After 3 weeks from the treatment, herbicidal effect of each test compound was investigated. The results are summarized in the following Table 6 wherein the ratings for evaluating herbicidal effects are the same as used in the Experiment 1, (1).

Table 6

| Test compound No. | Active ingredient amount g./are | Effect on crops | | | | Herbicidal effect | | | | |
|---|---|---|---|---|---|---|---|---|---|---|
|  |  | wheat | maiz | soy-bean | cotton | manna-grass | common purs-lane | white goose-foot | wild amaranth | chufa |
| 55 | 40 | 2 | 1 | 0 | 0 | 4 | 5 | 5 | 5 | 5 |
|  | 20 | 1 | 1 | 0 | 0 | 3 | 5 | 5 | 5 | 5 |
|  | 10 | 0 | 0 | 0 | 0 | 3 | 5 | 5 | 5 | 5 |
| 56 | 40 | 0 | 0 | 0 | 0 | 5 | 5 | 5 | 5 | 5 |
|  | 20 | 0 | 0 | 0 | 0 | 4 | 5 | 5 | 5 | 5 |
|  | 10 | 0 | 0 | 0 | 0 | 4 | 5 | 5 | 5 | 5 |
| 57 | 40 | 0 | 0 | 0 | 0 | 4 | 5 | 5 | 5 | 5 |
|  | 20 | 0 | 0 | 0 | 0 | 3 | 5 | 5 | 5 | 5 |
|  | 10 | 0 | 0 | 0 | 0 | 2 | 5 | 5 | 5 | 5 |
| 58 | 40 | 0 | 0 | 0 | 0 | 4 | 5 | 5 | 5 | 5 |
|  | 20 | 0 | 0 | 0 | 0 | 3 | 5 | 5 | 5 | 5 |
|  | 10 | 0 | 0 | 0 | 0 | 2 | 5 | 5 | 5 | 5 |
| 59 | 40 | 0 | 0 | 0 | 0 | 4 | 5 | 5 | 5 | 5 |
|  | 20 | 0 | 0 | 0 | 0 | 3 | 5 | 5 | 5 | 5 |
|  | 10 | 0 | 0 | 0 | 0 | 2 | 5 | 5 | 5 | 5 |
| 60 | 40 | 0 | 0 | 0 | 0 | 4 | 5 | 5 | 5 | 5 |
|  | 20 | 0 | 0 | 0 | 0 | 3 | 5 | 5 | 5 | 5 |
|  | 10 | 0 | 0 | 0 | 0 | 2 | 5 | 5 | 5 | 5 |
| 61 | 40 | 1 | 1 | 0 | 1 | 4 | 5 | 5 | 5 | 5 |
|  | 20 | 0 | 0 | 0 | 0 | 3 | 5 | 5 | 5 | 5 |
|  | 10 | 0 | 0 | 0 | 0 | 2 | 5 | 5 | 5 | 5 |
| 62 | 40 | 0 | 0 | 0 | 0 | 4 | 5 | 5 | 5 | 5 |
|  | 20 | 0 | 0 | 0 | 0 | 3 | 5 | 5 | 5 | 5 |
|  | 10 | 0 | 0 | 0 | 0 | 1 | 5 | 5 | 5 | 5 |
| 63 | 40 | 1 | 0 | 0 | 0 | 4 | 5 | 5 | 5 | 5 |
|  | 20 | 0 | 0 | 0 | 0 | 2 | 5 | 5 | 5 | 5 |
|  | 10 | 0 | 0 | 0 | 0 | 2 | 5 | 5 | 5 | 5 |
| 64 | 40 | 0 | 0 | 0 | 0 | 4 | 5 | 5 | 5 | 5 |
|  | 20 | 0 | 0 | 0 | 0 | 3 | 5 | 5 | 5 | 5 |
|  | 10 | 0 | 0 | 0 | 0 | 2 | 5 | 5 | 5 | 5 |
| 65 | 40 | 2 | 1 | 0 | 1 | 5 | 5 | 5 | 5 | 5 |
|  | 20 | 1 | 0 | 0 | 0 | 4 | 5 | 5 | 5 | 5 |
|  | 10 | 0 | 0 | 0 | 0 | 4 | 5 | 5 | 5 | 5 |
| 66 | 40 | 0 | 0 | 0 | 1 | 5 | 5 | 5 | 5 | 5 |
|  | 20 | 0 | 0 | 0 | 0 | 5 | 5 | 5 | 5 | 5 |
|  | 10 | 0 | 0 | 0 | 0 | 3 | 5 | 5 | 5 | 5 |
| 67 | 40 | 1 | 1 | 0 | 1 | 5 | 5 | 5 | 5 | 5 |
|  | 20 | 0 | 0 | 0 | 0 | 4 | 5 | 5 | 5 | 5 |
|  | 10 | 0 | 0 | 0 | 0 | 3 | 5 | 5 | 5 | 5 |
| 68 | 40 | 2 | 2 | 0 | 0 | 5 | 5 | 5 | 5 | 5 |
|  | 20 | 1 | 1 | 0 | 0 | 5 | 5 | 5 | 5 | 5 |
|  | 10 | 0 | 0 | 0 | 0 | 4 | 5 | 5 | 5 | 5 |
|  | 40 | 1 | 2 | 0 | 0 | 5 | 5 | 5 | 5 | 5 |

Table 6-continued

| Test compound No. | Active ingredient amount g./are | Effect on crops | | | | Herbicidal effect | | | | |
|---|---|---|---|---|---|---|---|---|---|---|
| | | wheat | maiz | soybean | cotton | manna-grass | common purslane | white goose-foot | wild amaranth | chufa |
| 69 | 20 | 1 | 1 | 0 | 0 | 4 | 5 | 5 | 5 | 5 |
| | 10 | 0 | 0 | 0 | 0 | 4 | 5 | 5 | 5 | 5 |
| | 40 | 0 | 0 | 0 | 2 | 5 | 5 | 5 | 5 | 5 |
| 70 | 20 | 0 | 0 | 0 | 1 | 4 | 5 | 5 | 5 | 5 |
| | 10 | 0 | 0 | 0 | 0 | 3 | 5 | 5 | 5 | 5 |
| | 40 | 0 | 0 | 0 | 0 | 4 | 5 | 5 | 5 | 5 |
| 71 | 20 | 0 | 0 | 0 | 0 | 3 | 5 | 5 | 5 | 5 |
| | 10 | 0 | 0 | 0 | 0 | 2 | 5 | 5 | 5 | 5 |
| | 40 | 0 | 0 | 0 | 0 | 4 | 5 | 5 | 5 | 5 |
| 72 | 20 | 0 | 0 | 0 | 0 | 2 | 5 | 5 | 5 | 5 |
| | 10 | 0 | 0 | 0 | 0 | 2 | 5 | 5 | 5 | 5 |
| | 40 | 1 | 0 | 0 | 0 | 4 | 5 | 5 | 5 | 5 |
| 73 | 20 | 0 | 0 | 0 | 0 | 3 | 5 | 5 | 5 | 5 |
| | 10 | 0 | 0 | 0 | 0 | 2 | 5 | 5 | 5 | 5 |
| | 40 | 1 | 1 | 0 | 1 | 5 | 5 | 5 | 5 | 5 |
| 74 | 20 | 0 | 0 | 0 | 0 | 4 | 5 | 5 | 5 | 5 |
| | 10 | 0 | 0 | 0 | 0 | 2 | 5 | 5 | 5 | 5 |
| | 40 | 0 | 0 | 0 | 1 | 4 | 5 | 5 | 5 | 5 |
| 75 | 20 | 0 | 0 | 0 | 0 | 3 | 5 | 5 | 5 | 5 |
| | 10 | 0 | 0 | 0 | 0 | 2 | 5 | 5 | 5 | 5 |

EXPERIMENT 4

Foliar treatment tests for upland weed control (1) Wagner pots, each having a surface of 1/5000 are, were packed with Ube soil and seedlings of manna-grass at 3 leaf stage, of cocklebur at 2 leaf stage, of white goose-foot at 2 leaf stage and of nutgrass at 3 leaf stage were planted and grown.

Then, a wettable powder of each test compound was diluted with water containing 100 ppm of "Neoesterin" (trade name of spreader available from Kumiai Kagaku K. K.) to a concentration of the active ingredient of 1000 ppm and the resulting preparation was uniformly applied to seedlings by foliar spraying under pressure at a dose of 5 ml. per pot. Then, the pots were kept in a glass chamber at an average temperature of approximately 25° C.

After 2 weeks from the treatment, herbicidal effects of each test compound were investigated.

The results are summarized in Table 7 wherein the same rating systems as in the Experiment 1, (1) were applied.

Table 7

| Test compound No. | Manna-grass | Cocklebur | White goose-foot | Nutgrass |
|---|---|---|---|---|
| 1 | 2 | 4 | 4 | 3 |
| 2 | 4 | 5 | 5 | 3 |
| 3 | 4 | 4 | 5 | 3 |
| 4 | 4 | 5 | 5 | 3 |
| 5 | 3 | 4 | 4 | 3 |
| 6 | 4 | 4 | 5 | 3 |
| 7 | 4 | 5 | 5 | 3 |
| 8 | 2 | 3 | 3 | 2 |
| 9 | 5 | 5 | 5 | 5 |
| 10 | 5 | 5 | 5 | 5 |
| 11 | 5 | 5 | 5 | 5 |
| 12 | 4 | 5 | 5 | 4 |
| 13 | 4 | 5 | 5 | 3 |
| 14 | 4 | 5 | 5 | 3 |
| 15 | 3 | 5 | 5 | 3 |
| 16 | 3 | 4 | 4 | 2 |
| 17 | 2 | 4 | 5 | 3 |
| 18 | 3 | 4 | 4 | 3 |
| 19 | 4 | 5 | 5 | 3 |
| 20 | 3 | 5 | 5 | 3 |
| 21 | 4 | 5 | 5 | 3 |
| 22 | 3 | 4 | 3 | 2 |
| 23 | 5 | 5 | 5 | 5 |
| 24 | 5 | 5 | 5 | 5 |
| 25 | 5 | 5 | 5 | 5 |
| 26 | 4 | 5 | 5 | 3 |
| 27 | 4 | 5 | 5 | 4 |
| 28 | 2 | 4 | 4 | 2 |
| 29 | 3 | 5 | 5 | 3 |
| 30 | 4 | 5 | 5 | 3 |
| 31 | 4 | 5 | 5 | 3 |
| 32 | 3 | 5 | 5 | 3 |
| 33 | 5 | 5 | 5 | 5 |
| 34 | 5 | 5 | 5 | 5 |
| 35 | 5 | 5 | 5 | 5 |
| 36 | 5 | 5 | 5 | 5 |
| 37 | 3 | 4 | 4 | 3 |
| 38 | 5 | 5 | 5 | 5 |
| 39 | 5 | 5 | 5 | 4 |
| 40 | 5 | 5 | 5 | 2 |
| 41 | 5 | 5 | 5 | 5 |
| 42 | 5 | 5 | 5 | 4 |
| 43 | 5 | 5 | 5 | 3 |
| 44 | 2 | 3 | 5 | 2 |
| 45 | 4 | 5 | 5 | 4 |
| 46 | 2 | 3 | 4 | 2 |
| 47 | 5 | 5 | 5 | 5 |
| 48 | 4 | 4 | 5 | 4 |
| 49 | 4 | 3 | 5 | 2 |
| 50 | 3 | 4 | 5 | 2 |
| 51 | 2 | 4 | 5 | 3 |
| 52 | 5 | 5 | 5 | 5 |
| 53 | 5 | 5 | 5 | 4 |
| 54 | 5 | 5 | 5 | 4 |
| NIP | 2 | 4 | 4 | 1 |

(2) Wagner pots, each having a surface of 1/5000 are were packed with upland soil, sowed with seeds of manna-grass, wild amaranth and white goose-foot and germination and growth were conducted in a glass chamber at 25° C. When manna-grass was at 3 leaf stage, wild amaranth at 2 leaf stage and white goose-foot at 2 leaf stage, each test compound was sprayed onto foliage at 5 ml./pot. The pots were kept for growth control in a glass chamber at 25° C. After 3 weeks from the treatment, herbicidal effect of each test compound was investigated. The results are summarized in the following Table 8 wherein the ratings for evaluating herbicidal effects are the same as used in the Experiment 1, (1).

Table 8

| Test compound No. | Active ingredient concentration % | manna-grass | wild amaranth | white goose-foot |
|---|---|---|---|---|
| 55 | 0.4 | 5 | 5 | 5 |
|  | 0.2 | 4 | 5 | 5 |
|  | 0.1 | 3 | 5 | 5 |
| 56 | 0.4 | 4 | 5 | 5 |
|  | 0.2 | 2 | 5 | 5 |
|  | 0.1 | 1 | 5 | 5 |
| 57 | 0.4 | 4 | 5 | 5 |
|  | 0.2 | 3 | 5 | 5 |
|  | 0.1 | 2 | 5 | 5 |
| 58 | 0.4 | 4 | 5 | 5 |
|  | 0.2 | 3 | 5 | 5 |
|  | 0.1 | 1 | 5 | 5 |
| 59 | 0.4 | 4 | 5 | 5 |
|  | 0.2 | 3 | 5 | 5 |
|  | 0.1 | 1 | 5 | 5 |
| 60 | 0.4 | 3 | 5 | 5 |
|  | 0.2 | 2 | 5 | 5 |
|  | 0.1 | 2 | 5 | 5 |
| 61 | 0.4 | 5 | 5 | 5 |
|  | 0.2 | 5 | 5 | 5 |
|  | 0.1 | 5 | 5 | 5 |
| 62 | 0.4 | 5 | 5 | 5 |
|  | 0.2 | 5 | 5 | 5 |
|  | 0.1 | 5 | 5 | 5 |
| 63 | 0.4 | 5 | 5 | 5 |
|  | 0.2 | 5 | 5 | 5 |
|  | 0.1 | 5 | 5 | 5 |
| 64 | 0.4 | 5 | 5 | 5 |
|  | 0.2 | 5 | 5 | 5 |
|  | 0.1 | 5 | 5 | 5 |
| 65 | 0.4 | 5 | 5 | 5 |
|  | 0.2 | 4 | 5 | 5 |
|  | 0.1 | 3 | 5 | 5 |
| 66 | 0.4 | 5 | 5 | 5 |
|  | 0.2 | 5 | 5 | 5 |
|  | 0.1 | 5 | 5 | 5 |
| 67 | 0.4 | 4 | 5 | 5 |
|  | 0.2 | 3 | 5 | 5 |
|  | 0.1 | 2 | 5 | 5 |
| 68 | 0.4 | 4 | 5 | 5 |
|  | 0.2 | 3 | 5 | 5 |
|  | 0.1 | 1 | 5 | 5 |
| 69 | 0.4 | 3 | 5 | 5 |
|  | 0.2 | 2 | 5 | 5 |
|  | 0.1 | 1 | 5 | 5 |
| 70 | 0.4 | 5 | 5 | 5 |
|  | 0.2 | 5 | 5 | 5 |
|  | 0.1 | 5 | 5 | 5 |
| 71 | 0.4 | 5 | 5 | 5 |
|  | 0.2 | 5 | 5 | 5 |
|  | 0.1 | 5 | 5 | 5 |
| 72 | 0.4 | 5 | 5 | 5 |
|  | 0.2 | 5 | 5 | 5 |
|  | 0.1 | 5 | 5 | 5 |
| 73 | 0.4 | 5 | 5 | 5 |
|  | 0.2 | 5 | 5 | 5 |
|  | 0.1 | 5 | 5 | 5 |
| 74 | 0.4 | 4 | 5 | 5 |
|  | 0.2 | 3 | 5 | 5 |
|  | 0.1 | 2 | 5 | 5 |
| 75 | 0.4 | 5 | 5 | 5 |
|  | 0.2 | 5 | 5 | 5 |
|  | 0.1 | 5 | 5 | 5 |

From the above-recited results, it can be seen that the diphenyl ether derivatives of this invention can effectively control a wide variety of weeds by soil or foliar application without any phytotoxicity to crops and thus are practically useful as an excellent herbicide.

We claim:

1. A compound having the formula

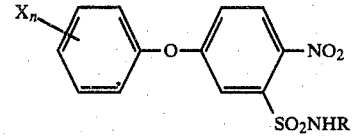

wherein X is a halogen atom or a trifluoromethyl group, n is an integer of 1 to 3 inclusive, and R is a hydrogen atom, a lower alkoxycarbonyl group, an acetyl group, a chloroacetyl group, an N,N-dimethylcarbamoyl group, a loweralkyl group, a lower-alkenyl group or a benzoyl group; and an alkali metal salt thereof.

2. A compound according to claim 1 wherein it is in the form of an alkali metal salt.

3. A compound according to claim 1 wherein $X_n$ is a 2,4-dichloro-, 2,4,6-trichloro-, 2,4-dichloro-6-fluoro-, 2-chloro-4-bromo-, 2-chloro-4-trifluoromethyl- or 2-bromo-4-trifluoromethyl-substituent.

4. A compound according to claim 1 wherein R is a hydrogen atom, an alkoxycarbonyl group having 1 to 3 carbon atoms in the alkoxy moiety, an acetyl group, a chloroacetyl group, an N,N-dimethylcarbamoyl group, an alkyl group having 1 to 4 carbon atoms, an alkenyl having 2 to 4 carbon atoms or a benzoyl group.

5. A herbicidal composition which comprises (i) as an active ingredient a herbicidally effective amount of a compound having the formula

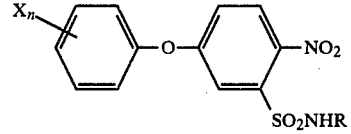

wherein X is a halogen atom or a trifluoromethyl group, n is an integer of 1 to 3 inclusive, and R is a hydrogen atom, a lower alkoxycarbonyl group, an acetyl group, a chloroacetyl group, an N,N-dimethylcarbamoyl group, a lower-alkyl group, a lower-alkenyl group or a benzoyl group; and an alkali metal salt thereof; and (ii) an agriculturally acceptable carrier.

6. A composition according to claim 5 wherein said active ingredient is in the form of an alkali metal salt.

7. A composition according to claim 5 wherein $X_n$ is a 2,4-dichloro, 2,4,6-trichloro-, 2,4-dichloro-6-fluoro-, 2-chloro-4-bromo-, 2-chloro-4-trifluoromethyl- or 2-bromo-4-trifluoromethyl-substituent.

8. A composition according to claim 5 wherein $R_1$ is a hydrogen atom, an alkoxycarbonyl group having 1 to 3 carbon atoms in the alkoxy moiety, an acetyl group, a chloroacetyl group, an N,N-dimethylcarbamoyl group, an alkyl group having 1 to 4 carbon atoms, an alkenyl group having 2 to 4 carbon atoms or a benzoyl group.

9. A composition according to claim 5 wherein said active ingredient is contained in an amount of 0.1–99% by weight, based upon the finished composition.

10. A process for the control of weeds which comprises applying to a locus to be protected, in an amount sufficient to exert a herbicidal action, a compound or an alkali metal salt thereof according to claim 1.

* * * * *

UNITED STATES PATENT AND TRADEMARK OFFICE
CERTIFICATE OF CORRECTION

PATENT NO. : 4,213,775
DATED : July 22, 1980
INVENTOR(S) : SHIGEKI NAGAI et al

It is certified that error appears in the above—identified patent and that said Letters Patent is hereby corrected as shown below:

Column 28, line 52: after "Urikawa", delete "0".

Column 29, Table 2: at "Test compound No. 16", "Dose g./are 50", in the fifth column of the table replace "3" with ---2---.

Column 43, Table 6: at "Test compound No. 74", "Active ingredient amount g./are 40", in the last column insert ---5--- in the blank space.

Signed and Sealed this

Sixth Day of January 1981

[SEAL]

Attest:

SIDNEY A. DIAMOND

Attesting Officer

Commissioner of Patents and Trademarks